United States Patent
Schreck

(10) Patent No.: US 9,757,262 B2
(45) Date of Patent: Sep. 12, 2017

(54) STENT GRAFT

(71) Applicant: Endologix, Inc., Irvine, CA (US)

(72) Inventor: Stefan G. Schreck, Fallbrook, CA (US)

(73) Assignee: Endologix, Inc., Irvine, CA (US)

( * ) Notice: Subject to any disclaimer, the term of this patent is extended or adjusted under 35 U.S.C. 154(b) by 537 days.

(21) Appl. No.: 13/943,246

(22) Filed: Jul. 16, 2013

(65) Prior Publication Data
US 2013/0304188 A1 Nov. 14, 2013

Related U.S. Application Data

(62) Division of application No. 12/837,398, filed on Jul. 15, 2010, now Pat. No. 8,491,646.

(Continued)

(51) Int. Cl.
A61F 2/82 (2013.01)
A61F 2/962 (2013.01)
(Continued)

(52) U.S. Cl.
CPC ............ *A61F 2/962* (2013.01); *A61F 2/07* (2013.01); *A61F 2/954* (2013.01); *A61F 2/966* (2013.01); *A61F 2/90* (2013.01); *A61F 2002/061* (2013.01); *A61F 2002/065* (2013.01); *A61F 2002/075* (2013.01); *A61F 2002/825* (2013.01); *A61F 2002/826* (2013.01)

(58) Field of Classification Search
CPC ........ A61F 2/07; A61F 2002/075; A61F 2/95; A61F 2/82
See application file for complete search history.

(56) References Cited

U.S. PATENT DOCUMENTS 2,127,903 A 8/1938 Bowen
2,437,542 A 5/1944 Krippendorf
(Continued)

FOREIGN PATENT DOCUMENTS

CA 2220141 11/1996
CA 2133530 1/1999
(Continued)

OTHER PUBLICATIONS

US 6,413,270, 07/2002, Thornton et al. (withdrawn)
(Continued)

*Primary Examiner* — Christopher D Prone
(74) *Attorney, Agent, or Firm* — Knobbe Martens Olson & Bear LLP

(57) ABSTRACT

Some embodiments are directed to a deployment system for deploying a stent graft within a passageway, including a delivery catheter having an outer sheath, a proximal end, and a distal end, a stent having a first end and a second end, a graft having a first end and a second end, and at least one connecting element extending from the second end of the stent to the first end of the graft so as to connect the stent to the graft. In some embodiments, the stent can be supported within the outer sheath at a first axial position in a collapsed state, and the graft can be supported within the outer sheath at a second axial position different than the first axial position in a collapsed state, such that the stent does not overlap or substantially overlap the graft in the collapsed state within the deployment system.

14 Claims, 15 Drawing Sheets

Related U.S. Application Data

(60) Provisional application No. 61/225,817, filed on Jul. 15, 2009.

(51) Int. Cl.
  A61F 2/07 (2013.01)
  A61F 2/954 (2013.01)
  A61F 2/966 (2013.01)
  A61F 2/06 (2013.01)
  A61F 2/90 (2013.01)

(56) References Cited

U.S. PATENT DOCUMENTS

| | | |
|---|---|---|
| 2,845,959 A | 8/1958 | Sidebotham |
| 2,990,605 A | 7/1961 | Demsyk |
| 3,029,819 A | 4/1962 | Starks |
| 3,096,560 A | 7/1963 | Liebig |
| 3,805,301 A | 4/1974 | Liebig |
| 4,362,156 A | 12/1982 | Feller, Jr. et al. |
| 4,473,067 A | 9/1984 | Schiff |
| 4,497,074 A | 2/1985 | Rey et al. |
| 4,501,263 A | 2/1985 | Harbuck |
| 4,503,568 A | 3/1985 | Madras |
| 4,525,157 A | 6/1985 | Vaillancourt |
| 4,562,596 A | 1/1986 | Kornberg |
| 4,580,568 A | 4/1986 | Gianturco |
| 4,592,754 A | 6/1986 | Gupte et al. |
| 4,617,932 A | 10/1986 | Kornberg |
| 4,756,307 A | 7/1988 | Crownshield |
| 4,800,882 A | 1/1989 | Gianturco |
| 4,816,028 A | 3/1989 | Kapadia et al. |
| 4,840,940 A | 6/1989 | Sottiurai |
| 4,856,516 A | 8/1989 | Hillstead |
| 4,878,906 A | 11/1989 | Lindemann et al. |
| 4,907,336 A | 3/1990 | Gianturco |
| 4,917,668 A | 4/1990 | Haindl |
| 4,922,905 A | 5/1990 | Strecker |
| 4,981,478 A | 1/1991 | Evard et al. |
| 4,981,947 A | 1/1991 | Tomagou et al. |
| 4,994,069 A | 2/1991 | Ritchrt et al. |
| 4,994,071 A | 2/1991 | MacGregor |
| 5,019,090 A | 5/1991 | Pinchuk |
| 5,035,706 A | 7/1991 | Giantureo et al. |
| 5,064,435 A | 11/1991 | Porter |
| 5,078,726 A | 1/1992 | Kreamer |
| 5,104,399 A | 4/1992 | Lazarus |
| 5,108,424 A | 4/1992 | Hoffman, Jr. et al. |
| 5,116,349 A | 5/1992 | Aranyi |
| 5,123,917 A | 6/1992 | Lee |
| 5,133,732 A | 7/1992 | Wiktor |
| 5,135,535 A | 8/1992 | Kramer |
| 5,135,536 A | 8/1992 | Hillstead |
| 5,156,619 A | 10/1992 | Ehrenfeld |
| 5,178,634 A | 1/1993 | Martinez |
| 5,197,976 A | 3/1993 | Herweck et al. |
| 5,201,757 A | 4/1993 | Heyn et al. |
| 5,211,658 A | 5/1993 | Clouse |
| 5,256,141 A | 10/1993 | Gencheff et al. |
| 5,275,622 A | 1/1994 | Lazarus et al. |
| 5,282,824 A | 2/1994 | Giantruco |
| 5,282,860 A | 2/1994 | Matsuno et al. |
| 5,304,200 A | 4/1994 | Spaulding |
| 5,314,444 A | 5/1994 | Gianturco |
| 5,314,472 A | 5/1994 | Fontaine |
| 5,316,023 A | 5/1994 | Palmaz et al. |
| 5,320,602 A | 6/1994 | Karpeil |
| 5,330,500 A | 7/1994 | Song |
| 5,342,387 A | 8/1994 | Summers |
| 5,354,308 A | 10/1994 | Simon et al. |
| 5,360,443 A | 11/1994 | Barone et al. |
| 5,366,504 A | 11/1994 | Andersen et al. |
| 5,370,683 A | 12/1994 | Fontaine |
| 5,387,235 A | 2/1995 | Chuter |
| 5,397,355 A | 3/1995 | Marin et al. |
| 5,405,377 A | 4/1995 | Cragg |
| 5,415,664 A | 5/1995 | Pinchuk |
| 5,423,886 A | 6/1995 | Arru et al. |
| 5,425,765 A | 6/1995 | Tiefenbrun et al. |
| 5,443,477 A | 8/1995 | Marin et al. |
| 5,443,498 A | 8/1995 | Fontaine |
| 5,443,500 A | 8/1995 | Sigwart |
| 5,458,615 A | 10/1995 | Klemm et al. |
| 5,462,530 A | 10/1995 | Jang |
| 5,464,450 A | 11/1995 | Buscemi et al. |
| 5,484,444 A | 1/1996 | Braunschweiler et al. |
| 5,489,295 A | 2/1996 | Piplani et al. |
| 5,496,365 A | 3/1996 | Sgro |
| 5,507,767 A | 4/1996 | Maeda et al. |
| 5,507,769 A | 4/1996 | Marin et al. |
| 5,507,771 A | 4/1996 | Gianturco |
| 5,522,880 A | 6/1996 | Barone et al. |
| 5,522,881 A | 6/1996 | Lentz |
| 5,522,883 A | 6/1996 | Slater et al. |
| 5,545,211 A | 8/1996 | An et al. |
| 5,554,118 A | 9/1996 | Jang |
| 5,554,181 A | 9/1996 | Das |
| 5,562,697 A | 10/1996 | Christiansen |
| 5,562,726 A | 10/1996 | Chuter |
| 5,562,728 A | 10/1996 | Lazarus et al. |
| 5,571,173 A | 11/1996 | Parodi |
| 5,575,816 A | 11/1996 | Rudnick et al. |
| 5,575,818 A | 11/1996 | Pinchuk |
| 5,578,071 A | 11/1996 | Parodi |
| 5,578,072 A | 11/1996 | Barone et al. |
| 5,591,197 A | 1/1997 | Orth et al. |
| 5,591,198 A | 1/1997 | Boyle et al. |
| 5,591,229 A | 1/1997 | Parodi |
| 5,591,230 A | 1/1997 | Horn et al. |
| 5,593,417 A | 1/1997 | Rhodes |
| 5,604,435 A | 2/1997 | Foo et al. |
| 5,607,445 A | 3/1997 | Summers |
| 5,609,625 A | 3/1997 | Piplani et al. |
| 5,609,627 A | 3/1997 | Goicoechea et al. |
| 5,609,628 A | 3/1997 | Keranen |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,630,830 A | 5/1997 | Verbeek |
| 5,632,763 A | 5/1997 | Glastra |
| 5,632,772 A | 5/1997 | Alcime et al. |
| 5,639,278 A | 6/1997 | Dereume et al. |
| 5,641,373 A | 6/1997 | Shannon et al. |
| 5,643,171 A | 7/1997 | Bradshaw et al. |
| 5,643,278 A | 7/1997 | Wijay |
| 5,647,857 A | 7/1997 | Anderson et al. |
| 5,649,952 A | 7/1997 | Lam |
| 5,651,174 A | 7/1997 | Schwartz et al. |
| 5,653,727 A | 8/1997 | Wiktor |
| 5,653,743 A | 8/1997 | Martin |
| 5,653,746 A | 8/1997 | Schmitt |
| 5,653,747 A | 8/1997 | Dereume |
| 5,662,580 A | 9/1997 | Bradshaw et al. |
| 5,662,614 A | 9/1997 | Edoga |
| 5,662,675 A | 9/1997 | Polanskyj Stockert et al. |
| 5,662,700 A | 9/1997 | Lazarus |
| 5,662,701 A | 9/1997 | Plaia et al. |
| 5,662,702 A | 9/1997 | Keranen |
| 5,662,703 A | 9/1997 | Yurek et al. |
| 5,665,115 A | 9/1997 | Cragg |
| 5,665,117 A | 9/1997 | Rhodes |
| 5,669,880 A | 9/1997 | Solar |
| 5,669,924 A | 9/1997 | Shaknovich |
| 5,669,934 A | 9/1997 | Sawyer |
| 5,674,241 A | 10/1997 | Bley et al. |
| 5,674,276 A | 10/1997 | Andersen et al. |
| 5,676,685 A | 10/1997 | Razavi |
| 5,676,696 A | 10/1997 | Marcade |
| 5,676,697 A | 10/1997 | McDonald |
| 5,679,400 A | 10/1997 | Tuch |
| 5,681,345 A | 10/1997 | Euteneuer |
| 5,681,346 A | 10/1997 | Orth et al. |
| 5,683,448 A | 11/1997 | Cragg |

(56) References Cited

U.S. PATENT DOCUMENTS

| | | |
|---|---|---|
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,683,453 A | 11/1997 | Palmaz |
| 5,690,642 A | 11/1997 | Osborne et al. |
| 5,690,643 A | 11/1997 | Wijay |
| 5,690,644 A | 11/1997 | Yurek et al. |
| 5,693,066 A | 12/1997 | Rupp et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,516 A | 12/1997 | Fischell et al. |
| 5,695,517 A | 12/1997 | Marin et al. |
| 5,697,948 A | 12/1997 | Marin et al. |
| 5,709,703 A | 1/1998 | Lukic et al. |
| 5,713,917 A | 2/1998 | Leonhardt |
| 5,716,365 A | 2/1998 | Goicoechea et al. |
| 5,716,393 A | 2/1998 | Lindenberg et al. |
| 5,718,724 A | 2/1998 | Goicoechea et al. |
| 5,718,973 A | 2/1998 | Lewis et al. |
| 5,720,735 A | 2/1998 | Dorros |
| 5,720,776 A | 2/1998 | Chuter et al. |
| 5,723,004 A | 3/1998 | Dereume et al. |
| 5,733,325 A | 3/1998 | Robinson et al. |
| 5,746,776 A | 5/1998 | Smith et al. |
| 5,749,880 A | 5/1998 | Banas et al. |
| 5,749,921 A | 5/1998 | Lenker et al. |
| 5,755,770 A | 5/1998 | Ravenscroft |
| 5,755,771 A | 5/1998 | Penn et al. |
| 5,755,777 A | 5/1998 | Chuter |
| 5,769,885 A | 6/1998 | Quiachon et al. |
| 5,769,887 A | 6/1998 | Brown et al. |
| 5,782,855 A | 7/1998 | Lau et al. |
| 5,782,909 A | 7/1998 | Quiachon et al. |
| 5,800,456 A | 9/1998 | Maeda et al. |
| 5,800,508 A | 9/1998 | Goicoechea et al. |
| 5,800,526 A | 9/1998 | Anderson et al. |
| 5,810,836 A | 9/1998 | Hussein et al. |
| 5,824,037 A | 10/1998 | Fogarty et al. |
| 5,824,039 A | 10/1998 | Piplani et al. |
| 5,824,040 A | 10/1998 | Cox et al. |
| 5,824,053 A | 10/1998 | Khosravi et al. |
| 5,843,160 A | 12/1998 | Rhodes |
| 5,843,162 A | 12/1998 | Inoue |
| 5,843,164 A | 12/1998 | Frantzen et al. |
| 5,843,167 A | 12/1998 | Dwyer et al. |
| 5,851,228 A | 12/1998 | Pinheiro |
| 5,855,599 A | 1/1999 | Wan |
| 5,860,998 A | 1/1999 | Robinson et al. |
| 5,867,432 A | 2/1999 | Toda |
| 5,868,783 A | 2/1999 | Tower |
| 5,871,536 A | 2/1999 | Lazarus |
| 5,879,321 A | 3/1999 | Hill |
| 5,879,366 A | 3/1999 | Shau et al. |
| 5,891,193 A | 4/1999 | Robinson et al. |
| 5,893,887 A | 4/1999 | Jayaraman |
| 5,902,334 A | 5/1999 | Dwyer et al. |
| 5,904,713 A | 5/1999 | Leschinsky |
| 5,906,640 A | 5/1999 | Penn et al. |
| 5,906,641 A | 5/1999 | Thompson et al. |
| 5,916,263 A | 6/1999 | Goicoechea et al. |
| 5,919,225 A | 7/1999 | Lau et al. |
| 5,925,075 A | 7/1999 | Myers et al. |
| 5,928,279 A | 7/1999 | Shannon et al. |
| 5,935,161 A | 8/1999 | Robinson et al. |
| 5,938,696 A | 8/1999 | Goicoechea et al. |
| 5,948,018 A | 9/1999 | Dereume et al. |
| 5,957,973 A | 9/1999 | Quiachon et al. |
| 5,961,546 A | 10/1999 | Robinson et al. |
| 5,961,548 A | 10/1999 | Shmulewitz |
| 6,001,125 A | 12/1999 | Golds et al. |
| 6,004,347 A | 12/1999 | McNamara et al. |
| 6,004,348 A | 12/1999 | Banas et al. |
| 6,017,363 A | 1/2000 | Hojeibane |
| 6,027,779 A | 2/2000 | Campbell et al. |
| 6,027,811 A | 2/2000 | Campbell et al. |
| 6,030,415 A | 2/2000 | Chuter |
| 6,039,749 A | 3/2000 | Marin et al. |
| 6,039,755 A | 3/2000 | Edwin et al. |
| 6,039,758 A | 3/2000 | Quiachon et al. |
| 6,045,557 A | 4/2000 | White et al. |
| 6,051,020 A | 4/2000 | Goicoechea et al. |
| 6,053,940 A | 4/2000 | Wijay |
| 6,063,113 A | 5/2000 | Kavteladze et al. |
| 6,070,589 A | 6/2000 | Keith et al. |
| 6,074,398 A | 6/2000 | Leschinsky |
| 6,077,296 A | 6/2000 | Shokoohi et al. |
| 6,077,297 A | 6/2000 | Robinson et al. |
| 6,086,611 A | 7/2000 | Duffy et al. |
| 6,090,128 A | 7/2000 | Douglas |
| 6,093,203 A | 7/2000 | Uflacker |
| 6,106,548 A | 8/2000 | Reubin et al. |
| 6,117,167 A | 9/2000 | Goicoechea et al. |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,168,610 B1 | 1/2001 | Marin et al. |
| 6,171,281 B1 | 1/2001 | Zhang |
| 6,183,481 B1 | 2/2001 | Lee et al. |
| 6,183,509 B1 | 2/2001 | Dibie |
| 6,187,036 B1 | 2/2001 | Shaolian |
| 6,192,944 B1 | 2/2001 | Greenhalgh |
| 6,197,049 B1 | 3/2001 | Shaolian et al. |
| 6,203,735 B1 | 3/2001 | Edwin et al. |
| 6,221,102 B1 | 4/2001 | Baker et al. |
| 6,231,563 B1 | 5/2001 | White et al. |
| 6,254,628 B1 * | 7/2001 | Wallace ............ A61B 17/1214 606/108 |
| 6,261,316 B1 | 7/2001 | Shaolian et al. |
| 6,273,909 B1 | 8/2001 | Kugler et al. |
| 6,280,466 B1 | 8/2001 | Kugler et al. |
| 6,280,467 B1 | 8/2001 | Leonhardt |
| 6,283,991 B1 | 9/2001 | Cox et al. |
| 6,344,054 B1 * | 2/2002 | Parodi ..................... A61F 2/962 623/1.13 |
| 6,348,066 B1 | 2/2002 | Pinchuk et al. |
| 6,350,278 B1 | 2/2002 | Lenker et al. |
| 6,352,553 B1 | 3/2002 | Van der Burg et al. |
| 6,352,561 B1 | 3/2002 | Leopold et al. |
| 6,355,060 B1 | 3/2002 | Lenker et al. |
| 6,361,557 B1 | 3/2002 | Gittings et al. |
| 6,361,637 B2 | 3/2002 | Martin et al. |
| 6,395,017 B1 | 5/2002 | Dwyer et al. |
| 6,395,018 B1 | 5/2002 | Castaneda |
| 6,395,019 B2 | 5/2002 | Chobotov |
| 6,398,807 B1 | 6/2002 | Chouinard et al. |
| 6,409,750 B1 | 6/2002 | Hyodoh et al. |
| 6,409,757 B1 | 6/2002 | Trout, III et al. |
| 6,416,474 B1 | 7/2002 | Penner et al. |
| 6,416,542 B1 | 7/2002 | Marcade et al. |
| 6,432,131 B1 | 8/2002 | Ravenscroft |
| 6,432,134 B1 | 8/2002 | Anson et al. |
| 6,464,721 B1 | 10/2002 | Marcade et al. |
| 6,475,166 B1 | 11/2002 | Escano |
| 6,475,170 B1 | 11/2002 | Doron et al. |
| 6,491,719 B1 | 12/2002 | Fogrty et al. |
| 6,500,202 B1 | 12/2002 | Shaolian et al. |
| 6,508,833 B2 | 1/2003 | Pavcnik et al. |
| 6,508,835 B1 | 1/2003 | Shaolian et al. |
| 6,511,325 B1 | 1/2003 | Lalka et al. |
| 6,514,281 B1 | 2/2003 | Blaeser et al. |
| 6,514,282 B1 | 2/2003 | Inoue |
| 6,517,572 B2 | 2/2003 | Kugler et al. |
| 6,517,573 B1 | 2/2003 | Pollock et al. |
| 6,520,988 B1 | 2/2003 | Colombo et al. |
| 6,524,335 B1 | 2/2003 | Hartley et al. |
| 6,533,811 B1 | 3/2003 | Ryan et al. |
| 6,551,350 B1 | 4/2003 | Thornton et al. |
| 6,558,396 B1 | 5/2003 | Inoue |
| 6,562,063 B1 | 5/2003 | Euteneurer et al. |
| 6,565,596 B1 | 5/2003 | White et al. |

(56) References Cited

U.S. PATENT DOCUMENTS

| | | |
|---|---|---|
| 6,565,597 B1 | 5/2003 | Fearnot et al. |
| RE38,146 E | 6/2003 | Palmaz et al. |
| 6,572,645 B2 | 6/2003 | Leonhardt |
| 6,576,009 B2 | 6/2003 | Ryan et al. |
| 6,582,460 B1 | 6/2003 | Cryer |
| 6,585,758 B1 | 7/2003 | Chouinard et al. |
| 6,592,614 B2 | 7/2003 | Lenker et al. |
| 6,592,615 B1 | 7/2003 | Marcade et al. |
| 6,613,073 B1 | 9/2003 | White et al. |
| 6,616,675 B1 | 9/2003 | Evard et al. |
| 6,652,579 B1 | 11/2003 | Cox et al. |
| 6,669,718 B2 | 12/2003 | Besselink |
| 6,733,523 B2 | 5/2004 | Shaolian et al. |
| 6,761,733 B2 | 7/2004 | Chobotov et al. |
| 6,767,359 B2 | 7/2004 | Weadock |
| 6,818,014 B2 | 11/2004 | Brown et al. |
| 6,821,292 B2 | 11/2004 | Pazienza et al. |
| 6,899,728 B1 | 5/2005 | Phillips et al. |
| 6,923,829 B2 | 8/2005 | Boyle et al. |
| 6,929,661 B2 | 8/2005 | Bolduc et al. |
| 6,932,837 B2 | 8/2005 | Amplatz et al. |
| 6,939,371 B2 | 9/2005 | Kugler et al. |
| 6,939,377 B2 | 9/2005 | Jayaraman et al. |
| 6,942,691 B1 | 9/2005 | Chuter |
| 6,942,692 B2 | 9/2005 | Landau et al. |
| 6,942,693 B2 | 9/2005 | Chouinard et al. |
| 6,953,475 B2 | 10/2005 | Shaolian et al. |
| 6,960,217 B2 | 11/2005 | Bolduc |
| 6,981,982 B2 | 1/2006 | Armstrong et al. |
| 6,984,244 B2 | 1/2006 | Perez et al. |
| 6,994,722 B2 | 2/2006 | DiCarlo |
| 7,004,964 B2 | 2/2006 | Thompson et al. |
| 7,004,967 B2 | 2/2006 | Chouinard et al. |
| 7,014,653 B2 | 3/2006 | Ouriel et al. |
| 7,025,779 B2 | 4/2006 | Elliott |
| 7,029,496 B2 | 4/2006 | Rakos et al. |
| 7,074,236 B2 | 7/2006 | Rabkin et al. |
| 7,105,017 B2 | 9/2006 | Kerr |
| 7,122,051 B1 | 10/2006 | Dallara et al. |
| 7,122,052 B2 | 10/2006 | Greenhalgh |
| 7,125,464 B2 | 10/2006 | Chobotov et al. |
| 7,160,318 B2 | 1/2007 | Greenberg et al. |
| 7,163,715 B1 | 1/2007 | Kramer |
| 7,175,652 B2 | 2/2007 | Cook et al. |
| 7,175,657 B2 | 2/2007 | Khan et al. |
| 7,189,256 B2 | 3/2007 | Smith |
| 7,201,770 B2 | 4/2007 | Johnson et al. |
| 7,235,095 B2 | 6/2007 | Haverkost et al. |
| 7,244,444 B2 | 7/2007 | Bates |
| 7,261,733 B1 | 8/2007 | Brown et al. |
| 7,264,631 B2 | 9/2007 | DeCarlo |
| 7,264,632 B2 | 9/2007 | Wright et al. |
| 7,267,685 B2 | 9/2007 | Butaric et al. |
| 7,270,675 B2 | 9/2007 | Chun et al. |
| 7,314,483 B2 | 1/2008 | Landau et al. |
| 7,320,703 B2 | 1/2008 | DiMatteo et al. |
| 7,402,168 B2 | 7/2008 | Acosta et al. |
| 7,435,253 B1 | 10/2008 | Hartley et al. |
| 7,491,230 B2 | 2/2009 | Holman et al. |
| 7,520,895 B2 | 4/2009 | Douglas et al. |
| 7,553,324 B2 | 6/2009 | Andreas et al. |
| 7,572,289 B2 | 8/2009 | Sisken et al. |
| 7,637,932 B2 | 12/2009 | Bolduc et al. |
| 7,651,519 B2 | 1/2010 | Dittman |
| 7,674,284 B2 | 3/2010 | Melsheimer |
| 7,691,135 B2 | 4/2010 | Shaolian et al. |
| 7,708,773 B2 | 5/2010 | Pinchuk et al. |
| 7,722,657 B2 | 5/2010 | Hartley |
| 7,833,259 B2 | 11/2010 | Boatman |
| 7,879,081 B2 | 2/2011 | DeMatteo et al. |
| 7,887,575 B2 | 2/2011 | Kujawski |
| 8,491,646 B2 | 7/2013 | Schreck |
| 2002/0049412 A1 | 4/2002 | Madrid et al. |
| 2003/0004560 A1 | 1/2003 | Chobotov et al. |
| 2003/0065375 A1 | 4/2003 | Eskuri |
| 2003/0074050 A1 | 4/2003 | Kerr |
| 2003/0097169 A1 | 5/2003 | Brucker et al. |
| 2003/0220682 A1 | 11/2003 | Kujawski |
| 2004/0073288 A1* | 4/2004 | Kerr .................. A61F 2/07 623/1.13 |
| 2004/0167618 A1 | 8/2004 | Shaolian et al. |
| 2004/0176832 A1 | 9/2004 | Hartley et al. |
| 2005/0038494 A1 | 2/2005 | Eidenschink |
| 2005/0058327 A1 | 3/2005 | Pieper |
| 2005/0059994 A1 | 3/2005 | Walak et al. |
| 2005/0060025 A1 | 3/2005 | Mackiewicz et al. |
| 2005/0080476 A1 | 4/2005 | Gunderson et al. |
| 2005/0113693 A1 | 5/2005 | Smith et al. |
| 2005/0113905 A1 | 5/2005 | Greenberg et al. |
| 2005/0119731 A1 | 6/2005 | Brucker et al. |
| 2005/0121120 A1 | 6/2005 | Van Dijk et al. |
| 2005/0131523 A1* | 6/2005 | Bashiri .................. A61F 2/90 623/1.15 |
| 2005/0159803 A1 | 7/2005 | Lad et al. |
| 2005/0165480 A1 | 7/2005 | Jordan et al. |
| 2005/0171598 A1 | 8/2005 | Schaeffer |
| 2005/0240153 A1 | 10/2005 | Opie |
| 2005/0240258 A1 | 10/2005 | Bolduc et al. |
| 2005/0240260 A1 | 10/2005 | Bolduc |
| 2006/0020320 A1 | 1/2006 | Shaolian et al. |
| 2006/0178733 A1 | 8/2006 | Pinchuk et al. |
| 2006/0233990 A1 | 10/2006 | Humphrey et al. |
| 2006/0233991 A1 | 10/2006 | Humphrey et al. |
| 2006/0271164 A1 | 11/2006 | Shaolian et al. |
| 2007/0203571 A1 | 8/2007 | Kaplan et al. |
| 2007/0213805 A1 | 9/2007 | Schaeffer et al. |
| 2007/0299497 A1 | 12/2007 | Shaolian et al. |
| 2008/0071343 A1 | 3/2008 | Mayberry et al. |
| 2008/0119890 A1 | 5/2008 | Adams et al. |
| 2008/0172122 A1 | 7/2008 | Mayberry et al. |
| 2008/0288044 A1 | 11/2008 | Osborne et al. |
| 2009/0099649 A1 | 4/2009 | Chobotov et al. |
| 2009/0138067 A1 | 5/2009 | Pinchuk et al. |
| 2009/0171437 A1 | 7/2009 | Brocker et al. |
| 2009/0177265 A1 | 7/2009 | Dierking et al. |
| 2009/0259298 A1 | 10/2009 | Mayberry et al. |
| 2010/0179636 A1 | 7/2010 | Mayberry et al. |
| 2010/0261662 A1 | 10/2010 | Schreck et al. |
| 2010/0280588 A1 | 11/2010 | Schreck |
| 2010/0318174 A1 | 12/2010 | Shaolian et al. |
| 2010/0318181 A1 | 12/2010 | Shaolian et al. |
| 2011/0022153 A1 | 1/2011 | Schreck et al. |
| 2011/0054586 A1 | 3/2011 | Mayberry et al. |
| 2011/0054587 A1 | 3/2011 | Mayberry et al. |
| 2011/0054594 A1 | 3/2011 | Mayberry et al. |

FOREIGN PATENT DOCUMENTS

| | | |
|---|---|---|
| DE | 295 21 548 U1 | 2/1995 |
| DE | 295 21 776 U1 | 2/1995 |
| EP | 0 177 330 B1 | 6/1991 |
| EP | 0 596 145 A1 | 5/1994 |
| EP | 0 621 015 A1 | 10/1994 |
| EP | 0 659 389 A1 | 6/1995 |
| EP | 0 688 545 | 12/1995 |
| EP | 0 689 806 A1 | 1/1996 |
| EP | 0 712 614 A1 | 5/1996 |
| EP | 0 732 088 A2 | 9/1996 |
| EP | 0 732 088 A3 | 9/1996 |
| EP | 0 740 928 A2 | 11/1996 |
| EP | 0 747 020 A2 | 12/1996 |
| EP | 0 775 470 A1 | 5/1997 |
| EP | 0 782 841 | 7/1997 |
| EP | 0 783 873 A2 | 7/1997 |
| EP | 0 783 874 A2 | 7/1997 |
| EP | 0 880 948 A1 | 12/1998 |
| EP | 0 904 745 A2 | 3/1999 |
| EP | 0 974 314 A2 | 1/2000 |
| EP | 0 732 088 B1 | 4/2000 |
| EP | 1 433 438 | 6/2004 |
| ES | 1 038 606 | 7/1998 |
| JP | 04-25755 | 1/1992 |
| JP | 08-336597 | 12/1996 |
| JP | 9-511160 | 11/1997 |

(56) References Cited

FOREIGN PATENT DOCUMENTS

| | | |
|---|---|---|
| JP | 2000-500047 | 1/2000 |
| WO | WO 93/13825 | 7/1993 |
| WO | WO 94/24961 | 11/1994 |
| WO | WO 95/21592 | 8/1995 |
| WO | WO 96/34580 | 11/1996 |
| WO | WO 96/39999 | 12/1996 |
| WO | WO 96/41589 | 12/1996 |
| WO | WO 97/10757 | 3/1997 |
| WO | WO 97/10777 | 3/1997 |
| WO | WO 97/14375 | 4/1997 |
| WO | WO 97/19652 | 6/1997 |
| WO | WO 97/26936 | 7/1997 |
| WO | WO 97/033532 | 9/1997 |
| WO | WO 97/045072 | 12/1997 |
| WO | WO 98/02100 | 1/1998 |
| WO | WO 98/53761 | 12/1998 |
| WO | WO 99/29262 | 6/1999 |
| WO | WO 99/44536 | 9/1999 |
| WO | WO 99/47077 | 9/1999 |
| WO | WO 99/58084 | 11/1999 |
| WO | WO 2005/037076 | 4/2005 |
| WO | WO 2005/107644 A1 | 11/2005 |
| WO | WO 2006/028925 | 3/2006 |

OTHER PUBLICATIONS

International Report on Patentability and Written Opinion re PCT/US2010/042181, dated Jan. 17, 2012.
U.S. Appl. No. 13/027,077, filed Feb. 14, 2011, Douglas et al.
U.S. Appl. No. 13/039,157, filed Mar. 2, 2011, Nguyen et al.
International Search Report in PCT Application No. PCT/US2010/042181 dated Mar. 31, 2011.

\* cited by examiner

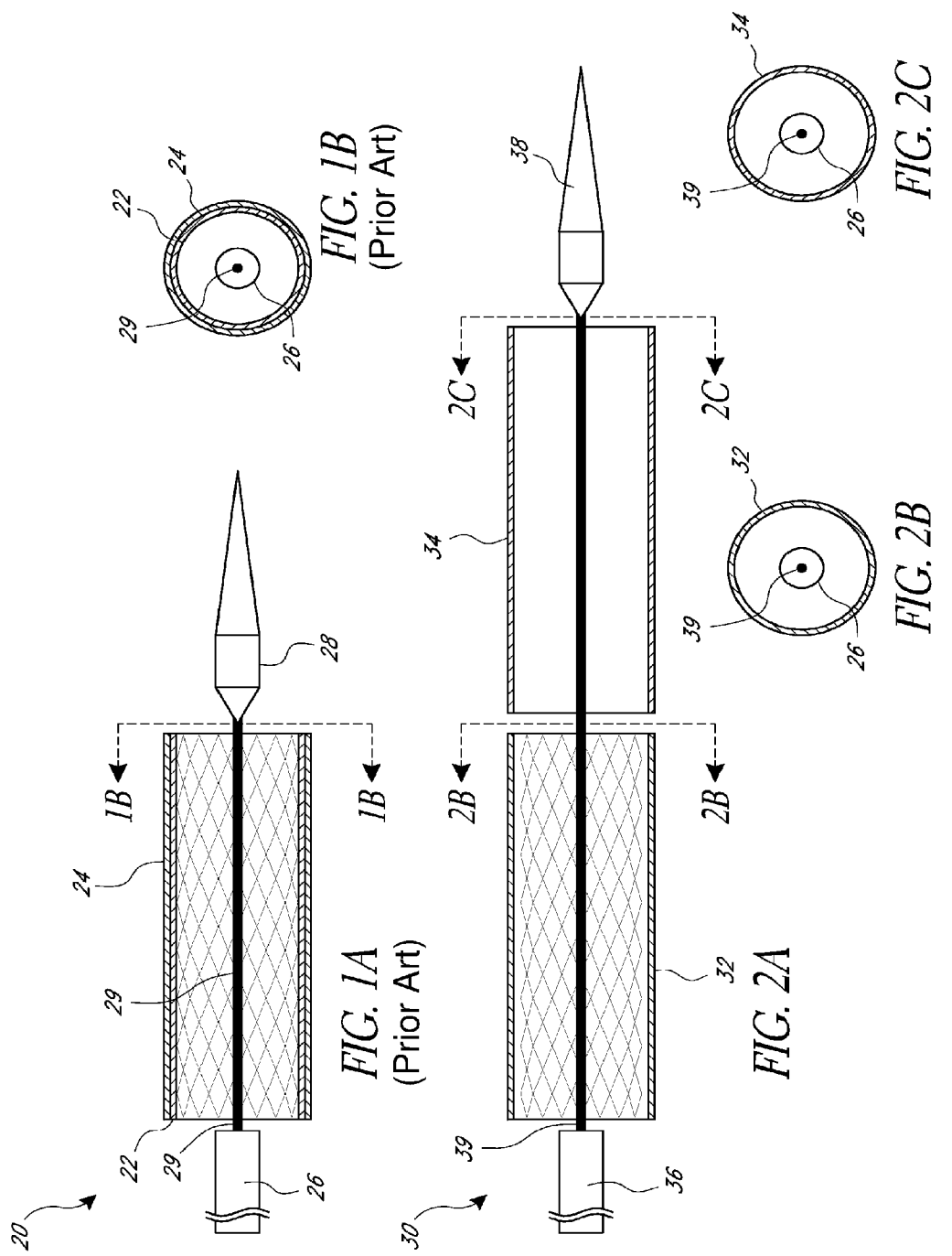

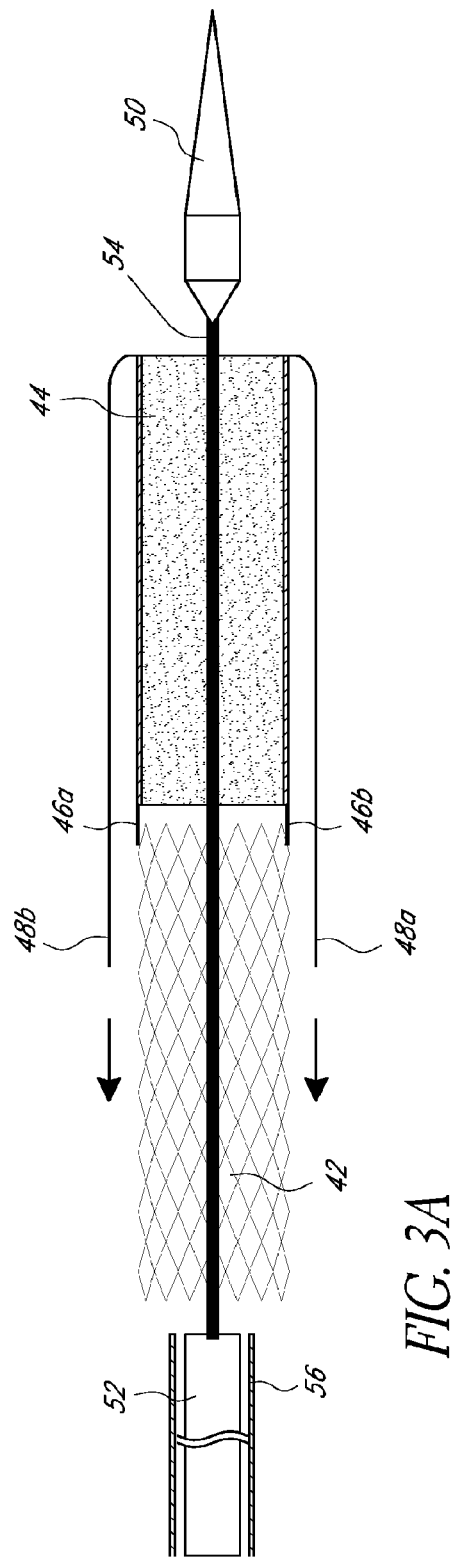
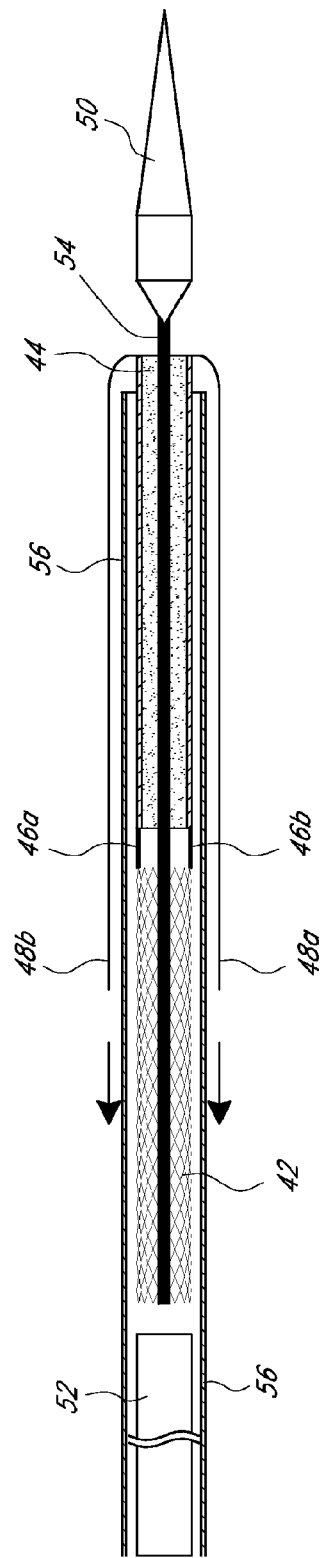
FIG. 3A
FIG. 3B

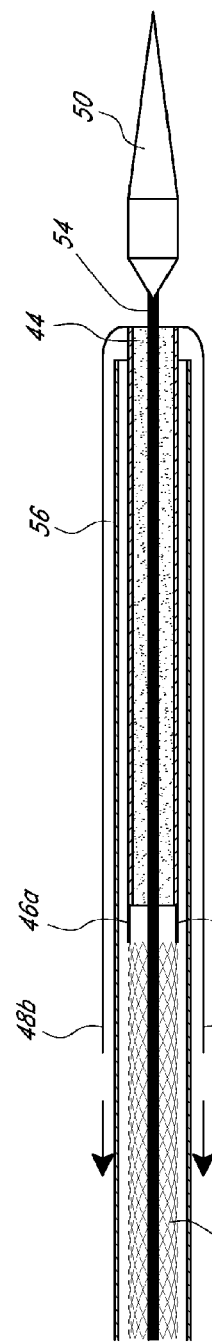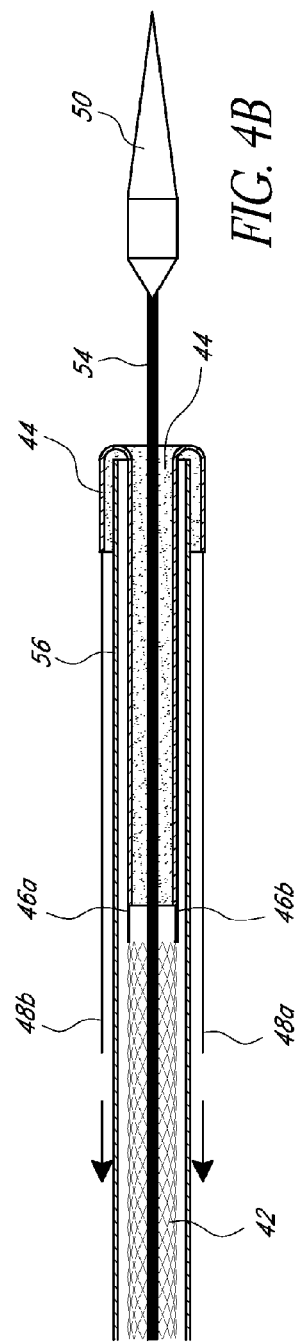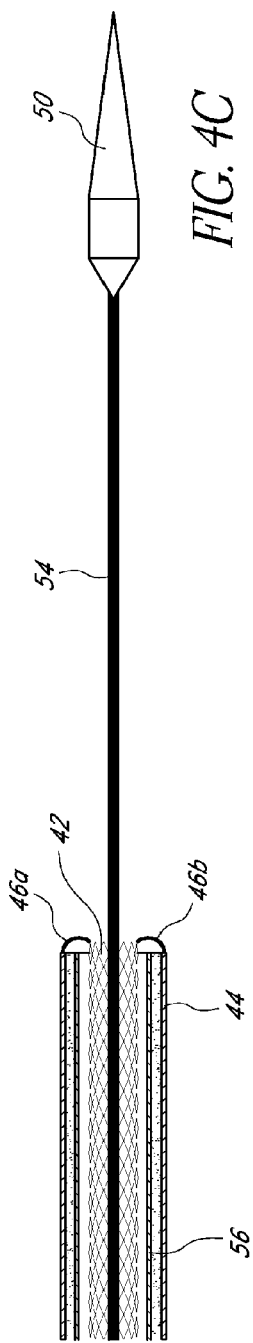

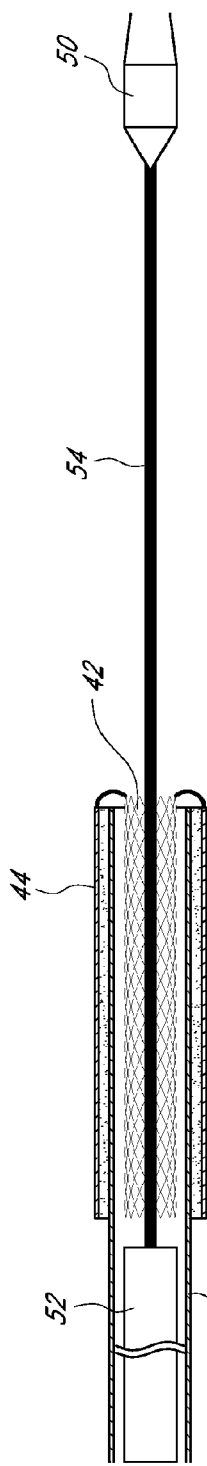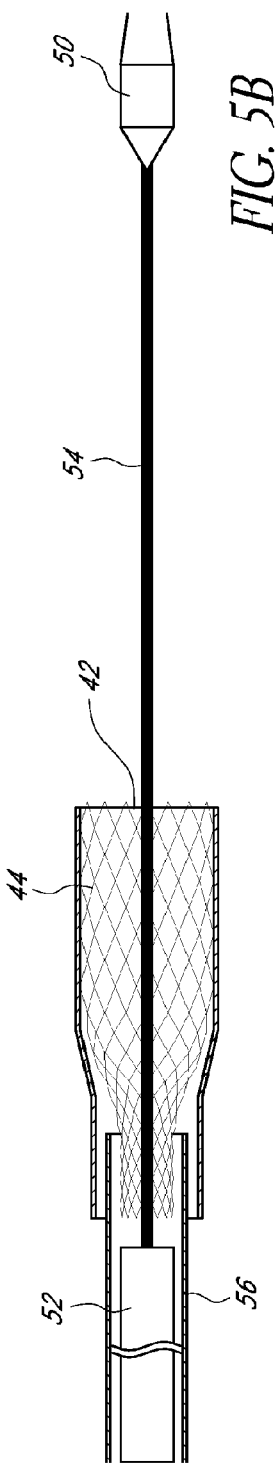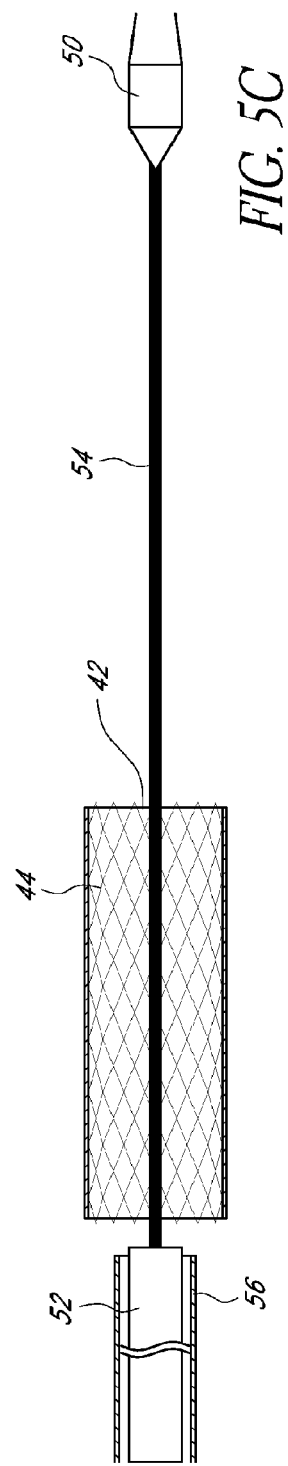

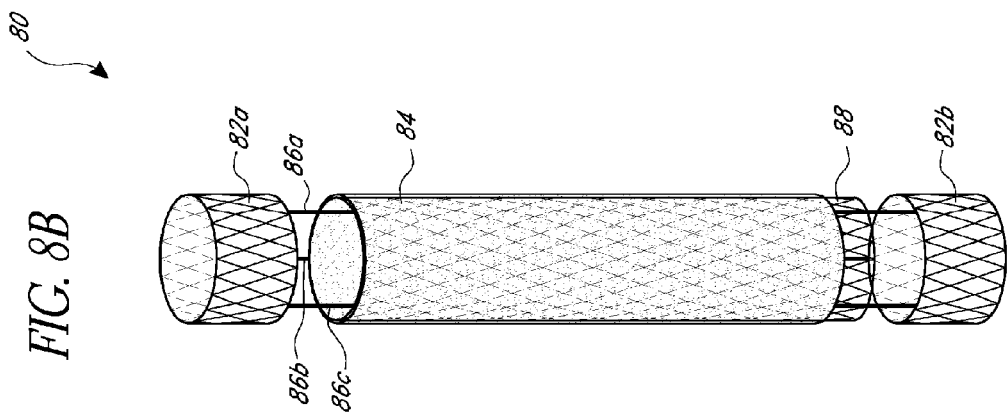
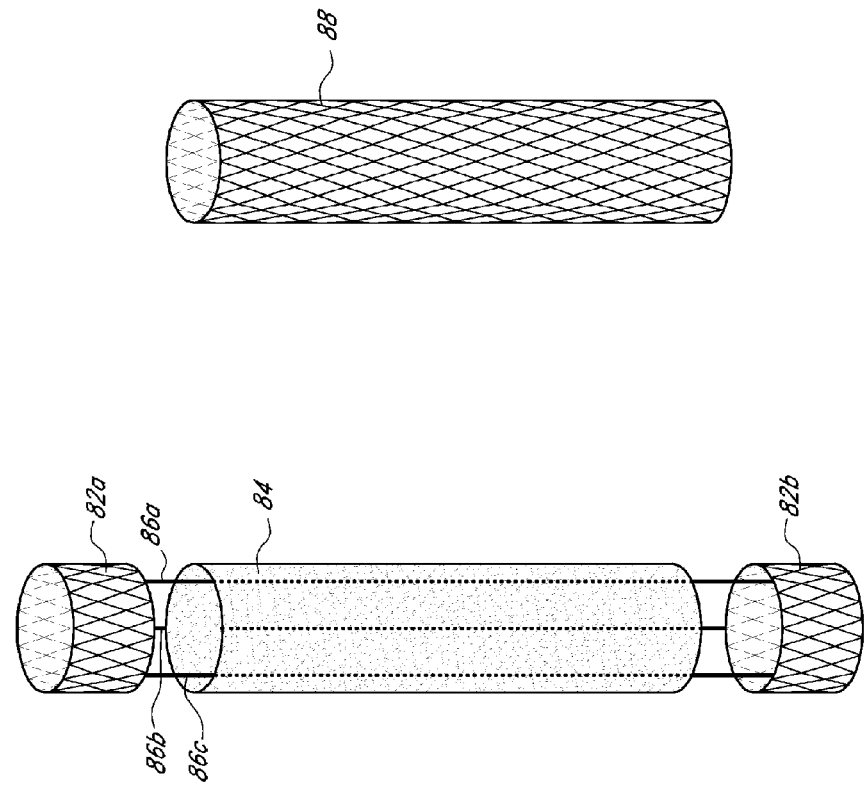

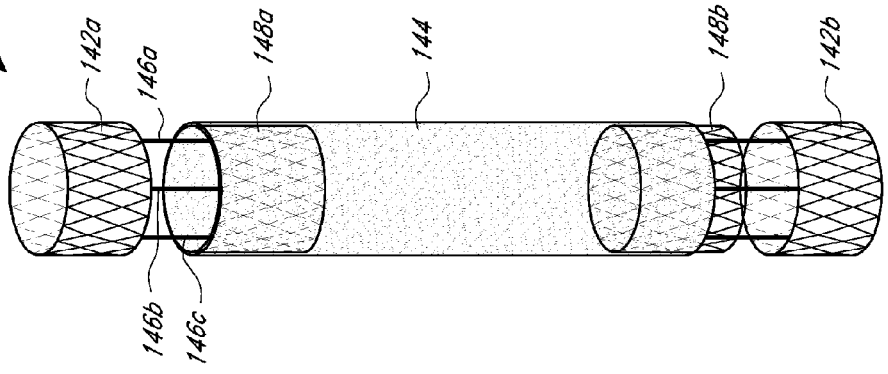
FIG. 11B
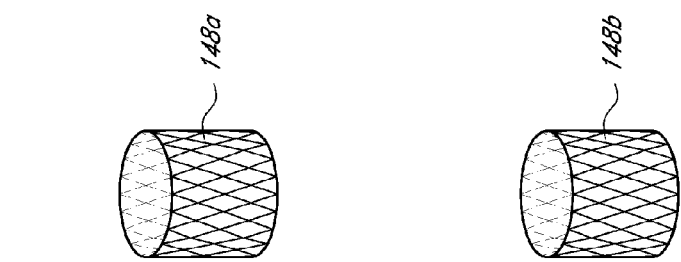
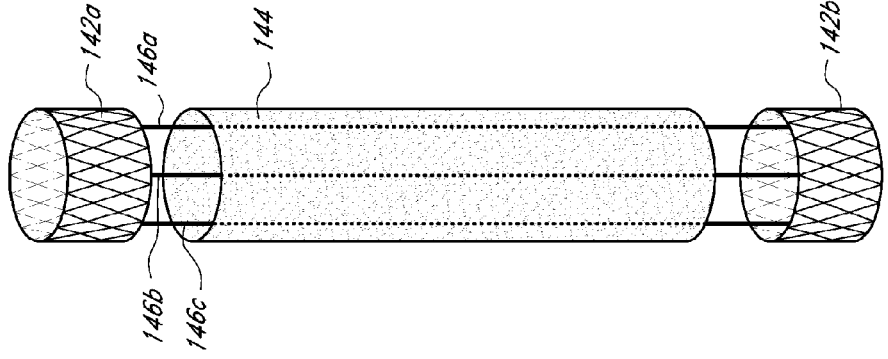
FIG. 11A

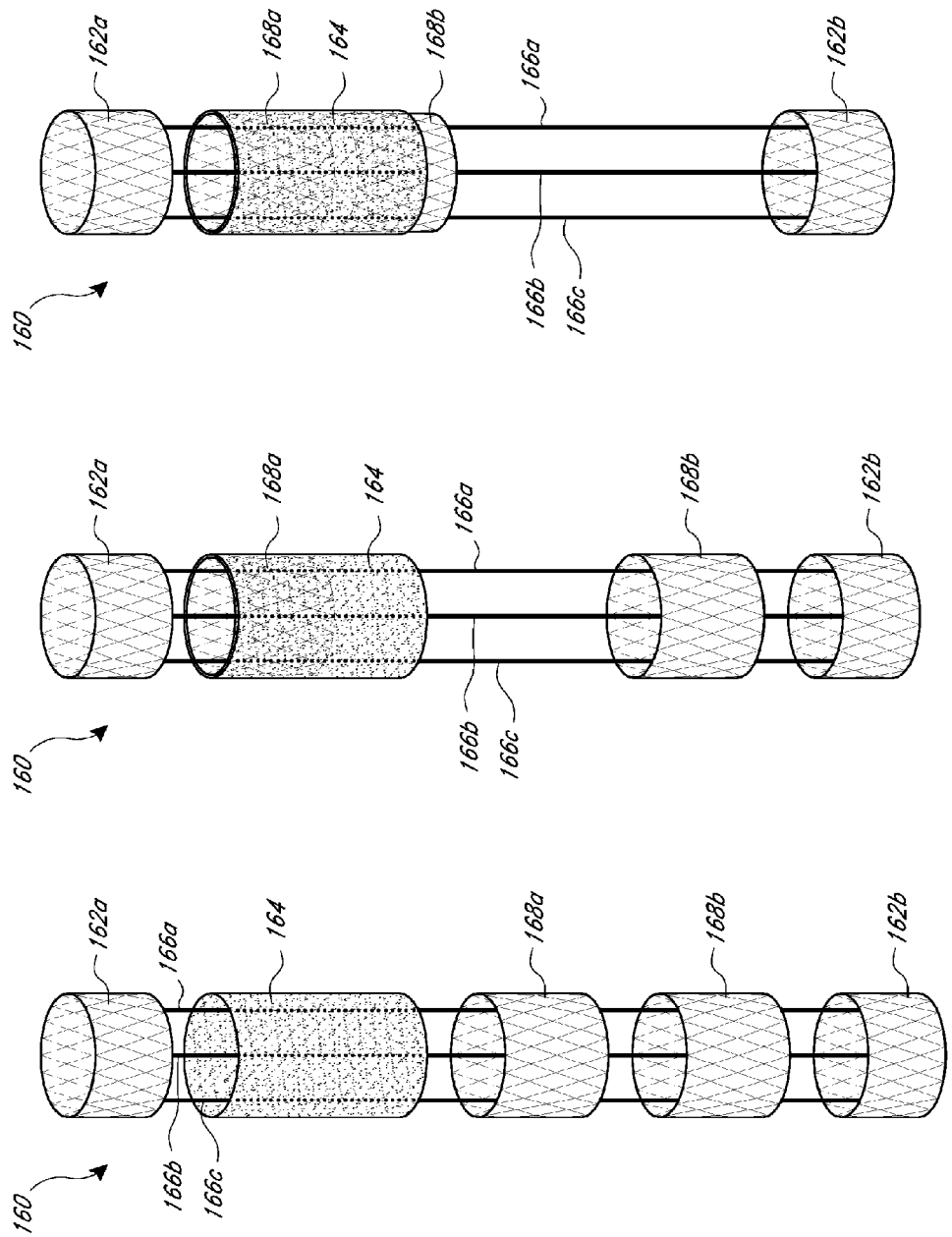

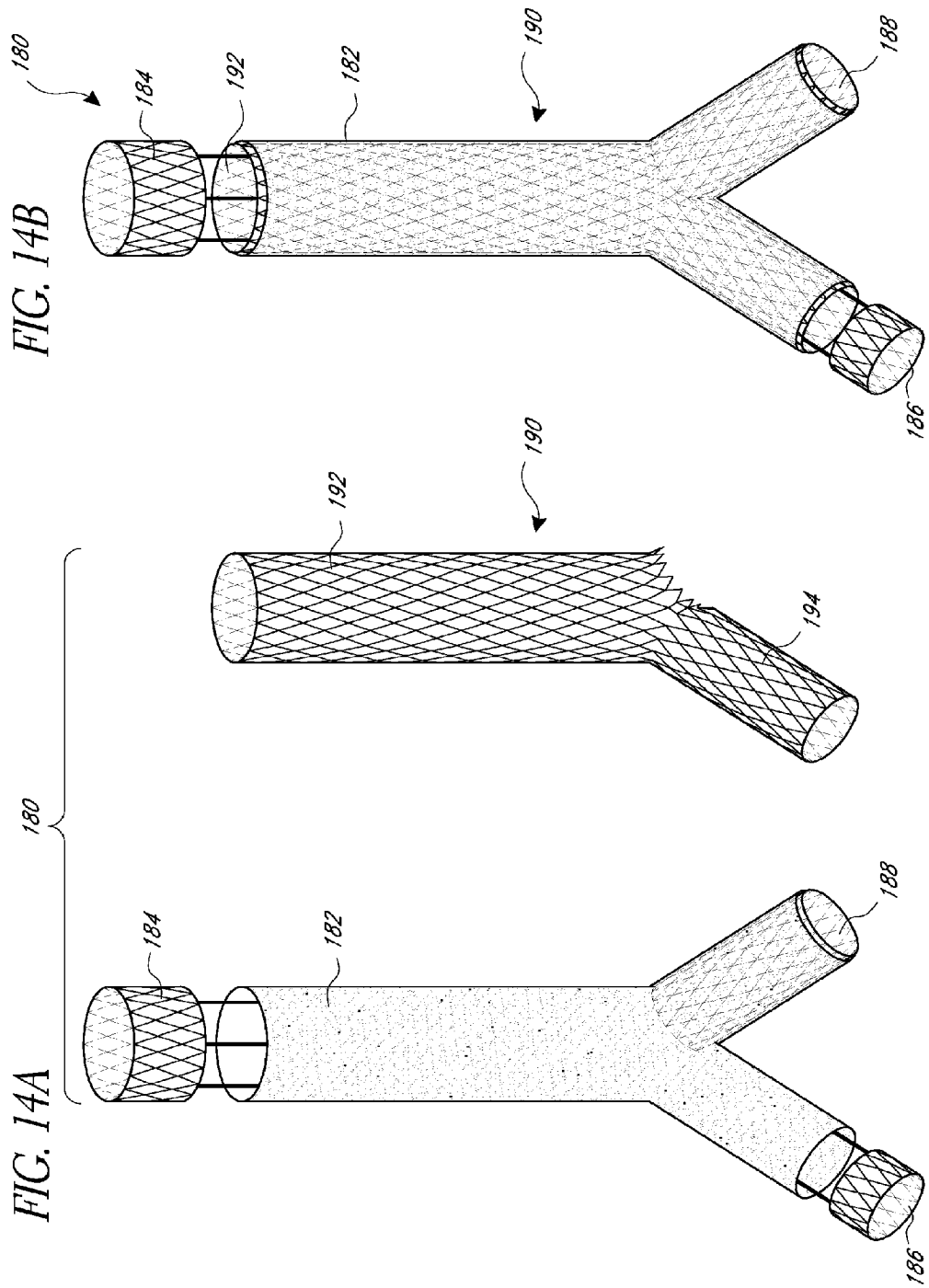

STENT GRAFT

PRIORITY INFORMATION AND INCORPORATION BY REFERENCE

This application is a divisional of U.S. patent application Ser. No. 12/837,398, now U.S. Pat. No. 8,491,646, filed on Jul. 15, 2010, which claims priority benefit under 35 U.S.C. §119(e) of U.S. Provisional Application 61/225,817 filed Jul. 15, 2009, each of which is incorporated by reference in its entirety herein. Additionally, U.S. Pat. No. 6,077,296 and U.S. patent application Ser. No. 12/101,863, filed on Apr. 11, 2008 (entitled "BIFURCATED GRAFT DEPLOYMENT SYSTEMS AND METHODS") are also hereby incorporated by reference in their entireties as if fully set forth herein.

BACKGROUND

Technical Field

The present disclosure relates to a stent graft or stent graft system that can be delivered in a low-profile catheter.

Background

Treatment of aortic diseases such as aneurysms and dissections include the placement of stent grafts to support the diseased vessel. Typically, these devices are delivered through a surgical incision into the femoral artery and advanced through the iliac artery into the aorta. The diameter of the aorta can range from approximately 15 mm to approximately 40 mm. Stent grafts of this diameter typically require delivery systems having an 18 Fr to a 25 Fr profile. Difficulties often are experienced in advancing these devices into the aorta because of the small access vessels including, for example, the iliac and femoral artery.

Thus, there is a clear need for a stent graft system that can be delivered by a low-profile delivery system.

SUMMARY OF SOME EMBODIMENTS

Some embodiments described herein are directed to systems, methods and apparatuses for treating endovascular aneurysms or other endovascular defects (collectively referred to as "aneurysms" or "defects"). However, it will be appreciated that the systems, methods and apparatuses can be used in other fields. In some embodiments, the defects being treated may include, but are not limited to, abdominal aortic aneurysms, subclavian aneurysms, thoracic aortic aneurysms, dissections, perforations, ulcers, and hematomas, to name a few.

In some embodiments, such defects can be treated with a deployment system for deploying an endoluminal prosthesis within a passageway comprising a graft supported in a first position within a catheter and a stent supported in a second position within the catheter and configured to be expandable within the graft, wherein the first position does not overlap the second position. The stent can be self-expandable, balloon expandable, or expandable by other suitable means.

Some embodiments are directed to an endoluminal prosthesis comprising a stent, a graft, and at least one connecting element in communication with the stent and the graft, the connecting element being supported by the stent and the graft, and being configured to provide axial support to the graft so that the graft is supported in a predetermined axial position relative to the stent. The stent can be self-expandable, balloon expandable, or expandable by other suitable means. In some embodiments, the stent and the graft can each be supportable in a collapsed position within the delivery catheter at different positions so that no portion of the stent overlaps any portion of the graft while the stent and graft are in the collapsed position within the delivery catheter.

In some embodiments, such defects can be treated using a method of making a endoluminal prosthesis delivery system, comprising supporting an endoluminal prosthesis in a collapsed position within a delivery catheter, the endoluminal prosthesis comprising a stent, a graft, and an axial support in communication with the stent and graft and configured to provide axial support at least between the stent and graft, and positioning the endoluminal prosthesis in the catheter body such that the stent is in a first position within the catheter and the graft is in a second position within the catheter, wherein the first position does not overlap the second position. Any stent disclosed herein can be self-expandable, balloon expandable, or expandable by other suitable means.

In some embodiments, such defects can be treated using a method of deploying an endoluminal prosthesis in a passageway, comprising supporting the endoluminal prosthesis in a collapsed position within an outer sleeve of a delivery catheter, the endoluminal prosthesis comprising a stent and a graft, positioning the stent and graft in the catheter such that the stent is in a first position within the catheter and the graft is in a second position within the catheter, wherein the first position does not overlap the second position, deploying the stent and graft from the catheter by axially retracting the outer sleeve of the catheter relative to the stent and graft so that at least the stent expands against a wall of the passageway, and axially supporting the graft with the stent so that the graft is supported in a predetermined axial position relative to the stent.

Some embodiments are directed to a deployment system for deploying a stent graft within a passageway, comprising a delivery catheter comprising an outer sheath, a proximal end, and a distal end, and a stent, a graft, and at least one connecting element in communication with the stent and the graft, the connecting element being supported by the stent and being configured to provide axial support to the graft so that the graft is supported in a predetermined axial position relative to the stent, wherein the stent and the graft are each supported in a collapsed position within the delivery catheter at different positions so that no portion of the stent overlaps any portion of the graft while the stent and graft are in the collapsed position within the delivery catheter.

Some embodiments are directed to a method of making a stent graft delivery system, comprising forming a stent and a graft, supporting the stent and the graft in a collapsed position in a delivery catheter such that no portion of the stent overlaps any portion of the graft. The stent can be self-expandable, balloon expandable, or expandable by other suitable means.

Some embodiments are directed to a deployment system for deploying a stent graft within a passageway, comprising a delivery catheter comprising an outer sheath, a proximal end, and a distal end, a stent having a first end and a second end, the stent being supported within the outer sheath at a first axial position in a collapsed state within the deployment system, a graft having a first end and a second end, the graft being supported within the outer sheath at a second axial position in a collapsed state within the deployment system, and at least one connecting element extending from the second end of the stent to the first end of the graft so as to connect the second end of the stent to the first end of the graft. In some embodiments, the second axial position can be different than the first axial position such that no substantial portion of the stent overlaps any portion of the graft while the stent and graft are in the collapsed state within the deployment system.

Some embodiments are directed to a deployment system for deploying a stent graft within a passageway, comprising a graft supported in a first axial position within a catheter, and a stent supported in a second axial position within the catheter and configured to be expandable within at least a portion of the graft. In some embodiments, the deployment system can be configured such that the graft in the first position does not axially overlap the stent in the second position when loaded within the catheter.

Some embodiments are directed to a method of deploying a stent graft comprising a stent and a graft in a passageway, comprising supporting the stent in a collapsed position in a first position within an outer sleeve of a delivery catheter, supporting the graft in a collapsed position in a second position within an outer sleeve of a delivery catheter, the second position being different than the first position such that no portion of the graft overlaps the stent, overlapping at least a portion of the stent with the graft, and expanding the stent against an inside surface of the graft within the passageway.

BRIEF DESCRIPTION OF THE DRAWINGS

These and other features, aspects and advantages of the present disclosure will now be described in connection with non-exclusive embodiments, in reference to the accompanying drawings. The illustrated embodiments, however, are merely examples and are not intended to be limiting. The following are brief descriptions of the drawings. The drawings may not be drawn to scale.

FIG. 1A is shows a conventional stent graft.

FIG. 1B is a section view of the conventional stent graft shown in FIG. 1A, taken through line 1B-1B of FIG. 1A.

FIG. 2A shows an embodiment of a low profile stent graft.

FIG. 2B is a section view of the embodiment of the stent graft shown in FIG. 2A, taken through line 2B-2B of FIG. 2A.

FIG. 2C is a section view of the embodiment of the stent graft shown in FIG. 2A, taken through line 2C-2C of FIG. 2A.

FIG. 3A shows an embodiment of a stent graft comprising a tubular stent and a tubular graft, before the stent and graft have been collapsed within the delivery catheter.

FIG. 3B shows the embodiment of the stent graft of FIG. 3A, after the stent and graft have been collapsed and supported within the delivery catheter.

FIG. 4A illustrates the embodiment of the stent graft deployment system of FIG. 3 before the outer sheath has been substantially retracted.

FIG. 4B illustrates the embodiment of the stent graft deployment system of FIG. 3 after the outer sheath has been partially retracted and the graft has been partially withdrawn from within the outer sheath by retracting the retraction elements of the deployment system.

FIG. 4C illustrates the embodiment of the stent graft deployment system of FIG. 3 after the outer sheath has been retracted proximally past the connecting elements and the graft has been substantially fully withdrawn from within the outer sheath by retracting the retraction elements.

FIG. 5A illustrates the embodiment of the stent graft deployment system of FIG. 3 after the retraction elements have been disconnected from the graft.

FIG. 5B illustrates the deployment of the embodiment of the stent of FIG. 3 within the graft.

FIG. 5C illustrates the embodiment of the stent of FIG. 3 fully deployed within the graft.

FIGS. 8A-8B illustrate another embodiment of a stent graft.

FIGS. 11A-11B illustrate another embodiment of a stent graft.

FIGS. 12A-12C illustrate another embodiment of a stent graft.

FIGS. 14A-14B illustrate another embodiment of a bifurcated stent graft.

DETAILED DESCRIPTION OF SOME EXEMPLIFYING EMBODIMENTS

Figure 6A:
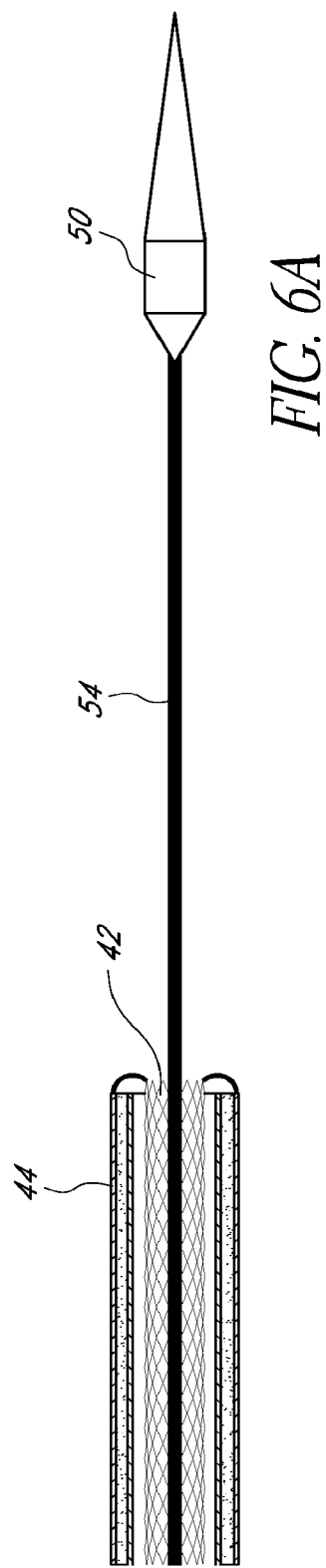
FIG. 6A illustrates an embodiment of the retractable tip extended distally away from the stent.

The following detailed description is now directed to some exemplifying embodiments. In this description, reference is made to the drawings wherein like parts are designated with like numerals throughout the description and the drawings.

Some embodiments described herein are directed to systems, methods, and apparatuses to treat lesions, aneurysms, or other defects (collectively referred to as "defects" or "aneurysms") in a patient's vasculature, including but not limited to the thoracic, ascending, and abdominal aorta, to name a few, or any other passageways, vessels, or areas of the body. In particular, some embodiments of this disclosure relate to novel designs of stent grafts or endoluminal prostheses that can be deployed by a low-profile or compact catheter based delivery system. Some embodiments of this disclosure pertain to a novel design of a stent graft catheter delivery system, and to methods of deploying the embodiments of the stent grafts or making the stent graft and stent graft delivery systems disclosed herein.

However, the systems, methods, and apparatuses disclosed herein can have application to other areas of the body or to other fields, and such additional applications are intended to form a part of this disclosure. For example, it will be appreciated that the systems, methods, and apparatuses may have application to the treatment of blood vessels in animals. In short, the embodiments and/or aspects of the stent grafts (also referred to herein as endoluminal prosthesis systems), methods, and apparatuses described herein can be applied to other parts of the body or may have other applications apart from the treatment of the thoracic, ascending, and abdominal aorta. Thus, while specific embodiments may be described herein with regard to particular portions of the aorta, it is to be understood that the embodiments described can be adapted for use in other portions of the aorta or other portions of the body or other applications altogether and are not limited to the aortic portions described.

FIG. 1A shows a conventional stent graft 20, and FIG. 1B is a section view of the conventional stent graft shown in FIG. 1A, taken through line 1B-1B of FIG. 1A. As illustrated therein, the stent graft 20 can have a tubular stent 22 which can be covered with a tubular graft 24. Such a stent is typically connected to the graft 24 on at least both ends of the stent 22, or along stent elements. Alternatively, the stent can be imbedded between two layers of graft material. The stent graft 20 is illustrated in an expanded state relative to a catheter with a shaft or core 26 and a tip 28 connected to the shaft 26 with a tube 29. When the stent graft 20 is crimped so as to be collapsed into a compressed state for delivery by the catheter, the graft 24 and stent 22 are typically co-located in the same space within the catheter so as to be axially aligned. Delivery catheters for conventional aortic stent grafts typically have a diameter of approximately 6-8 mm to accommodate the collapsed stent graft.

FIG. 2A shows an embodiment of a low profile stent graft 30. The stent graft 30 is illustrated in an expanded state relative to a catheter with a shaft or core 36 and a tip 38 connected to the shaft 36 with a tube 39. FIG. 2B is a section view of the embodiment of the stent graft 30 shown in FIG. 2A, taken through line 2B-2B of FIG. 2A. FIG. 2C is a section view of the embodiment of the stent graft 30 shown in FIG. 2A, taken through line 2C-2C of FIG. 2A. In the illustrated embodiment, or any other embodiment disclosed herein, the graft can be a straight tubular graft, a curved tubular graft, a multi-lumen graft, a bifurcated graft, a fenestrated graft, or any other suitable graft. Any of the configurations and details described with respect to the stent graft 30 can be applied to any of the other stent graft embodiments disclosed herein.

As illustrated therein, the stent 32 and the graft 34 can be separated and occupy different segments or axial portions of the delivery system between the shaft 36 and the tip 38. In some embodiments, the graft 34 can be loaded within the catheter so that no portion of the graft is radially supported by the stent 32. In some embodiments (not illustrated), a portion of the stent 32 and the graft 34 can overlap so that only a portion of the graft 34 is radially supported by the stent 32. For example, without limitation, in some embodiments, approximately 5% or less of the length of the graft can be supported by the stent 32. In some embodiments, from approximately 5% to approximately 10%, or from approximately 10% to approximately 25%, or more than approximately 25% of the length of the graft can be supported by the stent 32.

Accordingly, in some embodiments, the stent 32 and the graft 34 can be positioned in series in the delivery catheter. In some embodiments, the stent 32 and the graft 34 can be positioned within the catheter such that no substantial portion of the stent 32 overlaps a substantial portion of the graft 34. In some embodiments, as in the illustrated embodiment, the stent 32 and the graft 34 can be positioned within the catheter such that no portion of the stent 32 overlaps any portion of the graft 34. As a result, the diameter of the delivery system can be reduced for embodiments where the stent and graft are not overlapping or co-located within the delivery catheter. This basic design arrangement is applied to at least some of the following embodiments to create a low-profile stent graft system.

FIGS. 3A and 3B shows an embodiment of a stent graft deployment system 40 comprising a tubular stent 42 and a tubular graft 44. The stent 42 or any other stent or stent segment disclosed herein can be self-expandable, balloon expandable, or expandable by other suitable means. FIG. 3A shows the stent 42 and graft 44 before the stent 42 and graft 44 have been collapsed within the delivery catheter, and FIG. 3B shows the stent 42 and graft 44 after the stent 42 and graft 44 have been collapsed and supported within the delivery catheter. The stent 42 can be made from metal, preferably a memory alloy, or plastic, or any other material suitable for an expandable vascular stent. The graft 44 can be made from polyester, PTFE, ePTFE, polyurethane, silk, or any other material suitable for the vascular graft.

In some embodiments, the two components of the stent graft can be connected by connecting elements 46a, 46b (also referred to herein as axial supports). In some embodiments, the two components can be connected by two elements 46a, 46b as shown in FIGS. 3A and 3B, or, in some embodiments, only one element, or in some embodiments more than two elements. The connecting elements 46a, 46b can be at least laterally flexible and can comprise sutures, wires, strands, metal or plastic struts, or any other suitable components or materials. One or more retraction elements 48a, 48b can be connected to the proximal end of the graft 44 (i.e., the end of the graft 44 closest to the tip 50). The graft 44 can be attached to at least one retraction element 48a, 48b. In some embodiments, as shown in FIGS. 3A and 3B, the graft 44 preferably has at least two retraction elements. The retraction elements 48a, 48b can be sutures, cables, wires, or other similar or suitable components. To deliver the stent graft system into the body, the stent 44 and the graft 42 can be collapsed onto the catheter having a tip 50, a shaft 52 and a core or tubular wire 54. The stent 42 and graft 44 can be restrained by an outer sheath 56. In some embodiments, the one or more retraction elements 48a and 48b can be routed outside the outer sheath 56 to the proximal end of the catheter. In some embodiments, the one or more retraction elements 48a and 48b can through the main lumen within the outer sheath and/or through channels formed in an inner core of the catheter. Alternatively, the one or more retraction elements 48a and 48b can extend through lumen formed in the wall of the outer sheath 56 to the proximal end of the catheter.

FIGS. 4A to 5C illustrate the deployment of the embodiment of the stent graft deployment system 40 illustrated in FIGS. 3A and 3B. In particular, FIG. 4A illustrates the stent graft deployment system 40 before the outer sheath 56 has been substantially retracted. As illustrated, substantially all of the graft 44 is contained within the outer sheath 56 in FIG. 4A. FIG. 4B illustrates the stent graft deployment system 40 after the outer sheath 56 has been partially retracted and the graft 44 has been partially withdrawn from within the outer sheath 56 by retracting the retraction elements 48a, 48b. FIG. 4C illustrates the stent graft deployment system 40 after the outer sheath 56 has been retracted proximally past the connecting elements 46a, 46b, and the graft 44 has been substantially fully withdrawn from within the outer sheath 56 by retracting the retraction elements 48a, 48b.

With reference to FIGS. 4A-4C, once the catheter is inserted in the body, the outer sheath 56 can be retracted to release the graft 44. In some embodiments, the retraction elements 48a, 48b can be simultaneously retracted with the retraction of the sheath 56. The retraction elements 48a, 48b can pull the graft 44 over the sheath 56. In the process, in some embodiments, as in the illustrated embodiment, the graft 44 can be inverted as the graft 44 is being pulled over the sheath 56. When the graft 44 is fully released from the sheath 56, it can be positioned coaxial to the stent 42. In some embodiments, the connecting elements 46a, 46b can be configured to prevent the graft 44 from being pulled back beyond the tip of the stent 42. Additionally, in some embodiments, the stent 42 can have sufficient radial and axial strength or rigidity so as to prevent the graft 44 from being further retracted beyond the tip of the stent 42.

FIG. 5A illustrates the stent graft deployment system 40 after the retraction elements 48a, 48b have been disconnected from the graft 44. In some embodiments, the retraction elements 48a, 48b can be disconnected from the graft 44 by axially retracting the retraction elements 48a, 48b with sufficient force to sever the connection between the retraction elements 48a, 48b. For example, in some embodiments, the retraction elements 48a, 48b can be secured to the graft 44 using adhesive, sutures, or other similar materials or means, which can be configured to break or sever when a threshold axial force is exerted on the retraction elements 48a, 48b relative to the graft 44. In some embodiments, the retraction elements 48a, 48b may consist of sutures extending from the proximal end of the delivery system to the graft, looped through the end of the graft, and extending back to the proximal end of the delivery system. Release of one end of the suture and pulling on the other end of the suture allows the suture to release from the graft. In some embodiments, the retraction elements can be released from the graft 44 after completion of the procedure.

FIG. 5B illustrates the deployment of the stent 42 within the graft 44, after the graft 44 has been released from the outer sheath 56. In some embodiments, the stent 42 or any other stent embodiment disclosed herein can be self-expandable, mechanically expandable (such as a balloon expandable stent), or any other suitable stent. The stent 42 can expand to the diameter of the graft 44 and/or target vessel or passageway. The stent embodiment 42 illustrated in FIGS. 5A to 5C is self-expandable, self-expanding against the inside surface of the graft 44 as the outer sheath 56 is retracted in the direction indicated by the arrow. FIG. 5C illustrates the stent 42 fully deployed within the graft 44, which can be performed in a patient's aortic, thoracic, carotid, renal, or other suitable arteries or passageways within the body, including the cranial passageways. Once the stent 42 is completely expanded, the stent 42 and the graft 44 form a stent graft, and the some or all portions of the stent graft deployment system 40 can be removed from the patient.

Figure 6B:
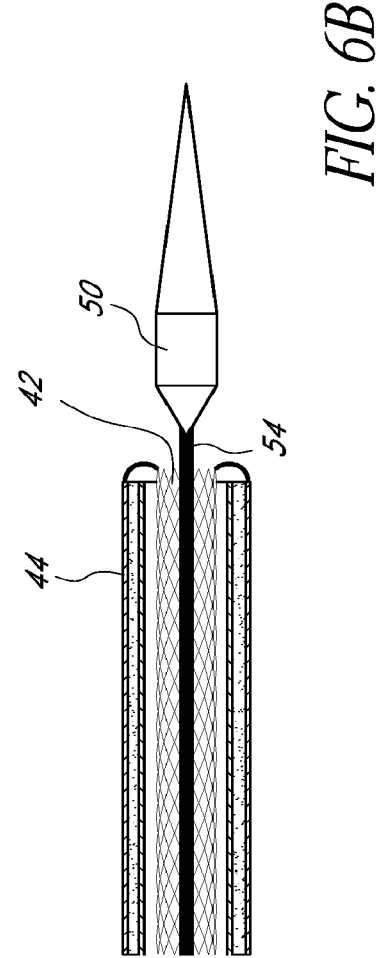
FIG. 6B illustrates the embodiment of the retractable tip retracted so as to be adjacent to the stent.

FIGS. 6A and 6B illustrates an embodiment of a retractable tip for use with some embodiments of the deployment catheters disclosed herein. FIG. 6A illustrates the embodiment of the retractable tip 50 extended distally away from the stent 42. FIG. 6B illustrates the embodiment of the retractable tip 50 retracted so as to be adjacent to the stent 42. With reference to these figures, in some embodiments, the tip 50 can be positioned substantially in front of (i.e., distally of) the stent 42. For placement of the stent in the thoracic aorta, the tip 50 can be advanced into the arch or the ascending aorta. To avoid potential complications from contact by the tip 50 or the leading edge of the stent 42 with a patient's vasculature, as illustrated in FIG. 6B, the tip 50 can be retracted to the stent 42 prior to advancing the stent to the target site.

The embodiments of the stent graft delivery system disclosed herein can have a lower-profile than those used for traditional stent graft designs. Another advantage of the proposed stent graft relates to the precise deployment of the stent graft, particularly in a high-flow environment. When traditional stent grafts are deployed, the flow can be obstructed by the graft during deployment. This is often referred to as "windsocking." Specifically, in the thoracic aorta, the fluid forces may push the graft distally, which can make it difficult to precisely deploy the stent graft. By first deploying the graft, the blood can pass through the graft unobstructed while the stent is being deployed, such as by the method of deployment of the embodiment of the stent graft illustrated in FIGS. 5A to 5C.

Figure 7B:
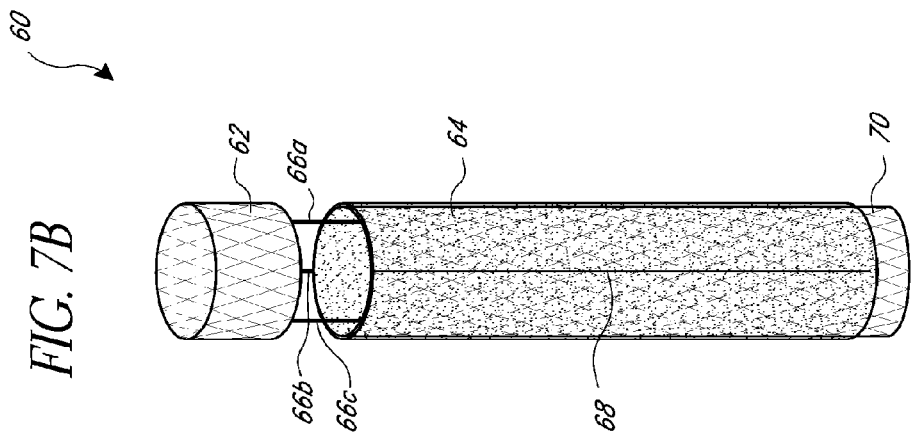
FIGS. 7A-7B illustrate another embodiment of stent graft.
Figure 7A:
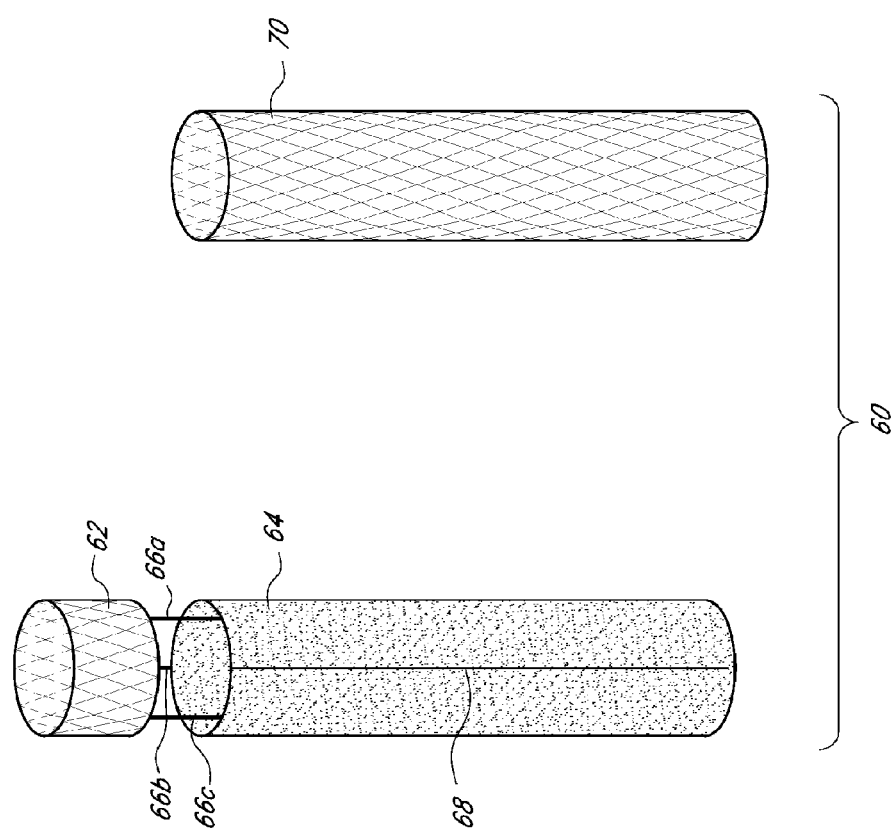

FIG. 7A illustrates another embodiment of a low-profile stent graft 60, before the illustrated components comprising the stent graft 60 have been combined. FIG. 7B illustrates the stent graft 60 shown in FIG. 7A after the illustrated components of the stent graft 60 have been combined. In some embodiments, a stent or stent segment 62 (also referred to herein as a first stent or stent element) can be connected to a graft 64 by means of connecting elements 66a, 66b, 66c. The stent or stent segment 62 can be self-expandable, balloon expandable, or expandable by other suitable means. Similar to the embodiment of the stent graft 30 discussed above, the stent 62 and graft 64 can be loaded into a catheter and restrained by a single sheath. In some embodiments, the stent 62 can be deployed before the graft 64 is deployed. The stent 62 can be deployed distally relative to the location of the graft 64 (i.e., further away from the end of the delivery catheter). The graft 64 can be deployed thereafter. The connecting elements 66a, 66b, 66c can be configured to support the graft 64 in a predetermined axial position relative to the stent 62 to prevent the graft from being displaced by the blood flow. In some embodiments, the connecting elements 66a, 66b, 66c can also provide radial support to the graft 64.

In some embodiments, one or more struts 68 or other suitable features (or any other struts disclosed herein) can be integrated in the graft 64 or attached thereto, such as by adhesive, sutures, or by other suitable means, to ensure that the graft 64 does not compress axially. In some embodiments, the struts 68 or any other struts disclosed herein can comprise sutures, wires, rods, or any other suitable components made from a polymer, metal, or other suitable material. In some embodiments, a second stent 70 can be delivered and deployed separately as compared to the stent 62 and graft 64 using a second delivery catheter, or can be delivered and deployed using the same delivery catheter as used to deploy the stent 62 and graft 64. The stent 70 can be deployed inside the graft 64 to further support the graft 64, thus forming the embodiment of the stent graft 60 shown in FIG. 7B.

FIG. 8A illustrates another embodiment of a low-profile stent graft 80, before all of the illustrated components of the stent graft 80 have been combined. FIG. 8B illustrates the stent graft 80 shown in FIG. 8A after all of the illustrated components of the stent graft 80 have been combined. In some embodiments, two stent segments 82a and 82b can be connected by axial struts 86a, 86b, 86c. The stent segments 82a and 82b can be self-expandable, balloon expandable, or expandable by other suitable means. The graft 84 can be mounted on the axial struts 86a, 86b, 86c to prevent the graft 84 from moving axially and to, in some embodiments, provide radial support. In some embodiments, the two stent segments 82a and 82b and the struts 86a, 86b, 86c can be manufactured from a single piece of metal tubing. Alternatively, in some embodiments, the struts 86a, 86b, 86c can be formed separately and supported by the stent segments 82a and 82b at any desired position relative to the stent segments 82a, 82b. The stent graft 80 can be deployed similarly to the previous embodiments, or by any suitable method.

The two stent segments 82a and 82b and struts 86a, 86b, 86c can support the graft 84 inside the blood vessel. In some embodiments, the axial struts 86a, 86b, 86c can expand the graft 84 to allow blood flow to pass through the lumen in the graft 84. In some embodiments, a second stent 88 can be deployed inside the graft 84 to effectively form the embodiment of the stent graft 80 shown in FIG. 8B. The second stent 88 can be delivered and deployed using the same delivery catheter as used to deploy the stent segments 82a, 82b, or can be deployed using a second delivery catheter.

Figure 9A:
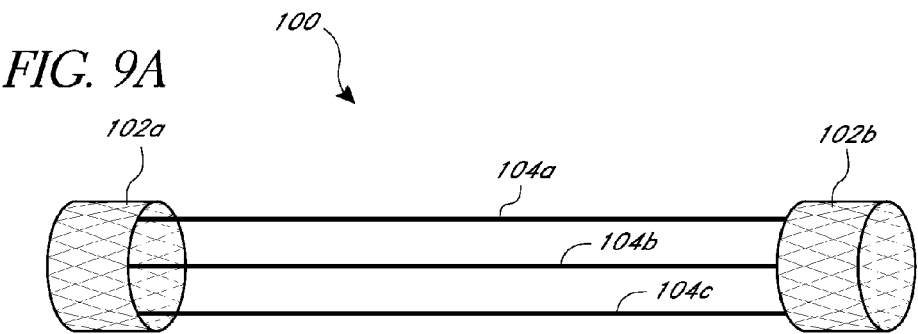
FIGS. 9A-9C illustrate another embodiment of a stent graft.

FIG. 9 illustrates another embodiment of a stent system 100. In some embodiments, the stent system 100 can be placed in curved blood vessels. As illustrated in FIG. 9A, the stent segments 102a, 102b can be directly connected by three struts 104a, 104b, 104c. The stent segments 102a and 102b can be self-expandable, balloon expandable, or expandable by other suitable means. In some embodiments, any number of struts 104 can be used, including one, two, three, four, or more struts. The struts 104 can be flexible so that the stent system 100 can bend to conform with curved vasculature.

Figure 9B:
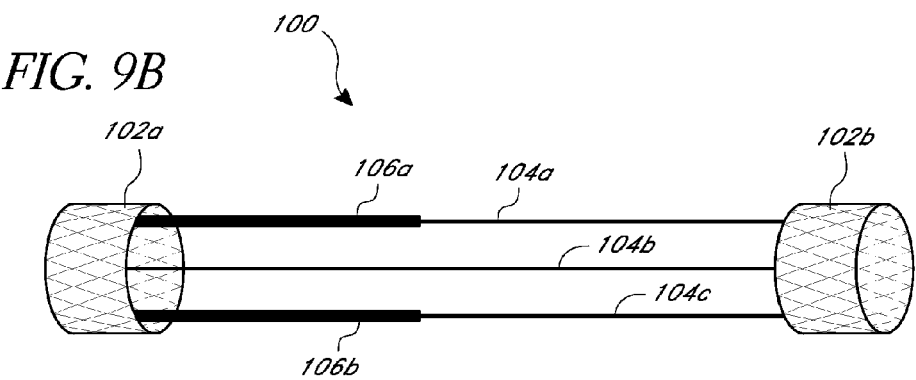
Figure 9C:
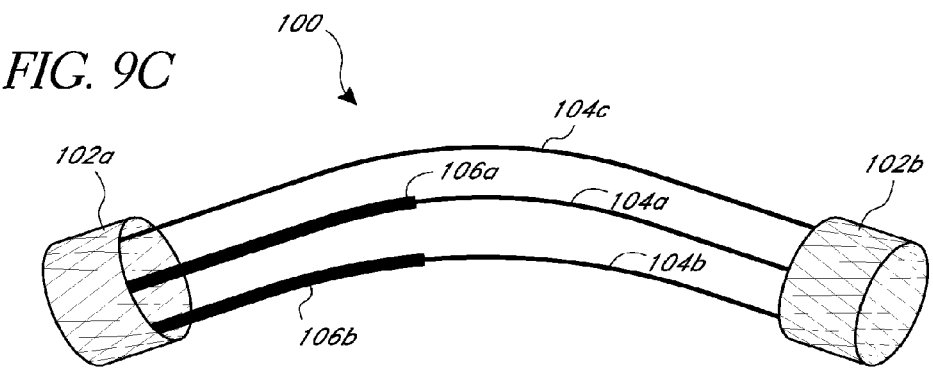
Figure 10:
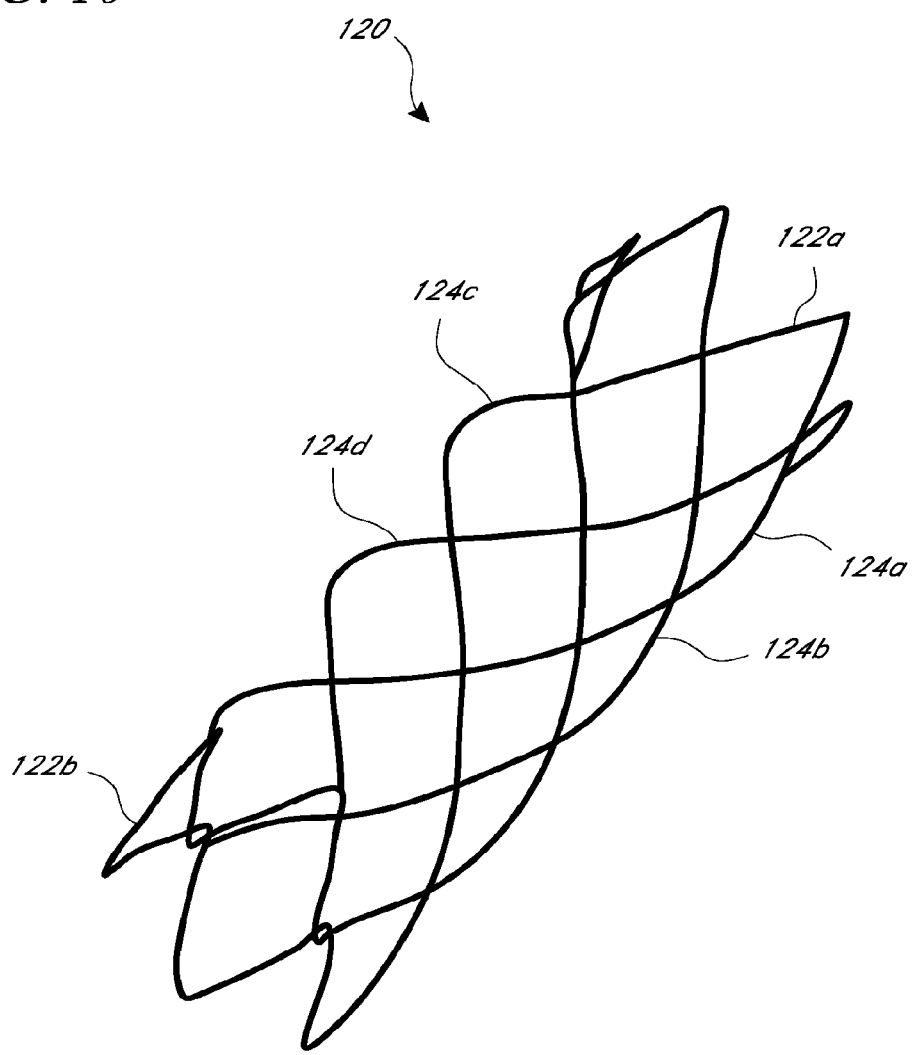
FIG. 10 illustrates another embodiment of a stent graft.

In some embodiments, as illustrated in FIG. 9B, the stent system 100 can be configured such that one, two, or less than all of the struts 104 (two being shown) are not directly connected to the stent segment 102a. The two struts 104a and 104b can terminate inside tubular struts 106a and 106b that can be connected to stent segment 102a. The struts 104a and 104b can move axially inside the tubular struts 106a and 106b, allowing the strut system to telescope. When the stent system 100 is placed in a curved vessel as shown in FIG. 9C, the telescoping struts can adjust their length and can arch between the two stent segments 102a, 102b. The stent system 100 can be deployed within any suitable graft. Furthermore, in some embodiments, the struts and tubular struts can have stops or otherwise can be configured so that the struts do not become inadvertently disengaged from the tubular struts after the stent system 100 has been deployed in the patient's vasculature. In some embodiments, the stent system 100 can be deployed within a graft, or can be deployed so as to have a graft supported thereon. In some embodiments, a graft (not illustrated) can be positioned over all or a portion of the stent system 100. A second stent (not illustrated) can be deployed within the stent system 100 after the stent system 100 has been deployed within a graft FIG. 10 illustrates another embodiment of a stent graft 120. The stent segments 122a and 122b can be connected by helical-shaped struts 124a-124d. The helical shape can allow the struts to conform to the curvatures in the blood vessel. Furthermore, the diameter of the stent graft at the location of the struts can be adjusted by rotating the stent segments 122a and 122b with respect to each other. The stent segments 122a and 122b can be self-expandable. Rotation in one direction can unwind the helical struts so as to increase the diameter of the helical segment. Rotation in the opposite direction can tighten the helical struts so as to decrease the diameter of the helical segment. The stent graft 120 can be deployed within any suitable grafts.

FIG. 11A illustrates another embodiment of a low-profile stent graft 140, before all of the illustrated components of the stent graft 140 have been combined. FIG. 11B illustrates the stent graft 140 shown in FIG. 11A after all of the illustrated components of the stent graft 140 have been combined. In some embodiments, the stent graft 140 can be similar to the stent graft 80 illustrated in FIGS. 8A and 8B, except as follows. Instead of one continuous stent, such as stent 88 in FIGS. 8A and 8B, being deployed within the stent graft 140, individual stent segments 148a, 148b can be placed inside the graft 144 to seal the ends of the graft 144 against the vessel wall. The stent segments 148a and 148b can be self-expandable, balloon expandable, or expandable by other suitable means. In some embodiments, the stent segments 148a, 148b can be deployed inside the graft 144 after the stents 142a, 142b have been deployed. In some embodiments, the stent segments 148a, 148b can be deployed inside the struts 146a, 146b, 146c after the stents 142a, 142b have been deployed so as to apply a radial outward force on the graft 144 and the struts 146a, 146b, 146c.

FIG. 12 illustrates another embodiment of a stent graft 160. In particular, FIG. 12A illustrates an embodiment of the stent graft 160 with stent segments in a first position, FIG. 12B illustrates an embodiment of the stent graft 160 with stent segments in a second position, and FIG. 12C illustrates an embodiment of the stent graft 160 with stent segments in a third position. In some embodiments, the stent graft 160 can be the same as or similar to the stent graft 140, except as follows. As illustrated in FIG. 12A, the individual stent segments 168a and 168b can be pre-mounted onto the struts 166a, 166b, 166c. The stent segments 168a and 168b can be self-expandable, balloon expandable, or expandable by other suitable means. The struts 166a, 166b, and 166C can also function as a guide for the deployment of the individual stent segments 168a and 168b. The struts 166a, 166b, and 166C can be configured to keep the individual stent segments 168a and 168b aligned with the central axis of the stent graft and prevent the individual stent segments 168a and 168b from tilting during deployment.

The struts 166 or any other struts disclosed herein can be positioned at any desired location relative to the stents 168a, 168b or any other stents disclosed herein. In some embodiments, the stent segments 168a, 168b can be supported by the struts 166a, 166b, 166c so that the stent segments 168a, 168b are positioned on the outside of the struts 166a, 166b, 166c. Alternatively, the stent segments 168a, 168b can be supported by the struts 166a, 166b, 166c so that the stent segments 168a, 168b are positioned on the inside of the struts 166a, 166b, 166c, or so that at least a portion of each of the stent segments 168a, 168b is positioned on the inside of the struts 166a, 166b, 166c and such that at least a portion of each of the stent segments 168a, 168b is positioned on the outside of the struts 166a, 166b, 166c.

In some embodiments, at least a portion of the graft 164 can be axially and/or radially supported by the struts 166a, 166b, 166c so that the graft 164 is maintained in a fixed axial position relative to the struts 166a, 166b, 166c. Alternatively, in some embodiments, at least a portion of the graft 164 can be supported by the stent 162a and/or by one or more connecting elements or other suitable connecting means so that the graft 164 is maintained in a fixed axial position relative to the stent 162a. The stent segments 168a, 168b can be supported by the struts 166a, 166b, 166c so that the stent segments 168a, 168b are axially moveable relative to the struts 166a, 166b, 166c and relative to the graft 164. In some embodiments, the stent segments 168a, 168b can be loaded into and deployed from the same delivery system as the graft 164 and the stent graft 162a, 162b, 166a, 166b, 166c. In some embodiments, the stent segments 168a, 168b can be axially positioned and deployed inside the graft 164 after the stents 162a, 162b have been deployed in the target vessel. Furthermore, the stent segments 168a, 168b can be deployed in a controlled fashion by restraining and then releasing the struts 166a, 166b, 166c.

Figure 13:
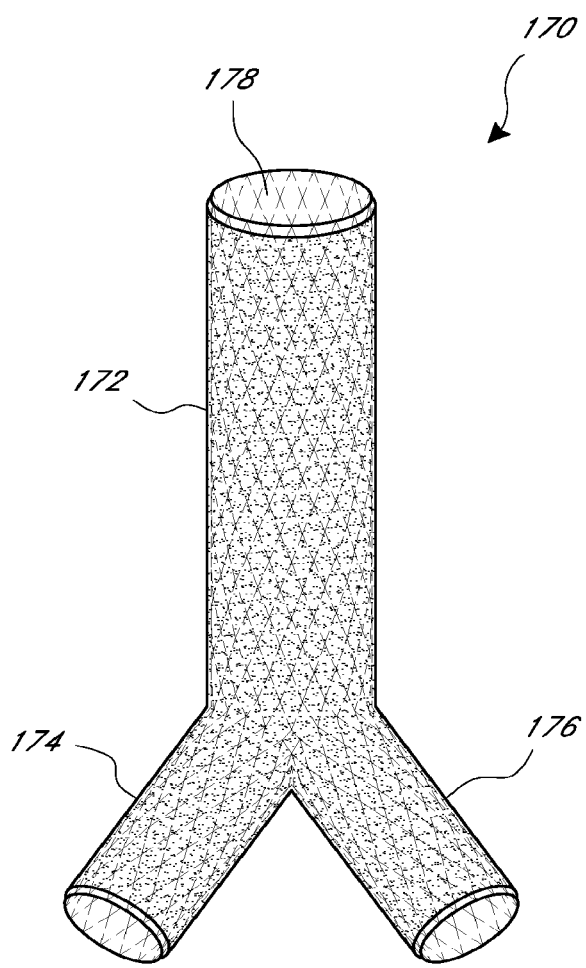
FIG. 13 illustrate an embodiment of a bifurcated stent graft.

The proposed concept of a low-profile stent graft or stent graft system can also be applied to bifurcated stent grafts. Accordingly, any of the embodiments of the stent systems or stent graft systems disclosed above can be modified so as to be a bifurcated stent or stent graft system. Bifurcated stent grafts can be used for the treatment of aorto-iliac aneurysms that require a proximal seal in the infrarenal aorta and distal seals in the iliac arteries. FIG. 13 illustrates an embodiment of a typical bifurcated stent graft 170 having a bifurcated graft having a main body graft 172 and two branch grafts 174, 176. As illustrated, a bifurcated stent 178 can be deployed inside the bifurcated graft.

FIGS. 14A and 14B illustrates another embodiment of a bifurcated stent graft 180. In particular, FIG. 14A illustrates the components of an embodiment of a stent graft 180 before the components of the stent graft 180 have been merged. FIG. 14B illustrates the embodiment of a stent graft 180 after the components of the stent graft 180 have been merged. In some embodiments, initially, the bifurcated graft 181, which can comprise a main graft body 182, a first branch portion 183, and a second branch portion 185, can be supported by three separate stent segments or elements 184, 187, 188. Stent segment or element 184 can be connected to the proximal end of the main graft body 182 similarly as compared to the embodiment of the straight stent graft shown in FIGS. 7A and 7B. Similarly, a second stent segment or element 187 can be connected to the distal end of a first or an ipsilateral branch graft 183 of the graft 181. A third stent segment or element 188 can be supported inside a second or a contralateral branch graft 185. The stent segments 184, 187, 188 or any stents, stent segments, or stent elements disclosed herein can be self-expandable, balloon expandable, or expandable by other suitable means.

The stent graft 180 can be configured such that, when the stent graft is collapsed into a crimped state for loading into a delivery catheter, the stents 184, 187, 188 are positioned at non-overlapping axial positions in the delivery catheter so that the stents 184, 187, 188 will not compete with each user for space in the catheter. In some embodiments, after the bifurcated graft 182 and the stents 184, 187, 188 are deployed in the target location, a second stent 190 having a main body stent 192 and a branch stent 194 can be deployed inside the bifurcated graft 182 to provide support along the entire length of the graft 182, as shown in FIG. 14B. The stent graft 180 can be configured such that the stent graft 180 comprises any of a wide varying combination or configuration of stents, stent segments, or graft segments.

FIGS. 15A to 16B illustrate the deployment of an embodiment of the bifurcated stent graft 180 in an abdominal aortic aneurysm. Two renal arteries 200a, 200b, iliac arteries 202a, 202b, an aortic aneurysm 206, and an aortic bifurcation 204 are illustrated. The illustrated aortic aneurysm 206 extends between the renal arteries 200a, 200b and the iliac arteries 202a, 202b. In some embodiments, the bifurcated stent graft can be delivered from a first artery, which can be the ipsilateral iliac artery 202b, and placed on the aortic bifurcation 204. The main stent segment 184 and connecting elements 186 supported by the main stent segment 184 can support the main graft body 182 in the target location. Additionally, in some embodiments, as illustrated in FIGS. 15A to 16B, the main graft body 182 can be positioned in the patient's vasculature so as to not obstruct the renal arteries 200a, 200b, so that blood can freely flow into the renal arteries 200a, 200b.

Figure 15B:
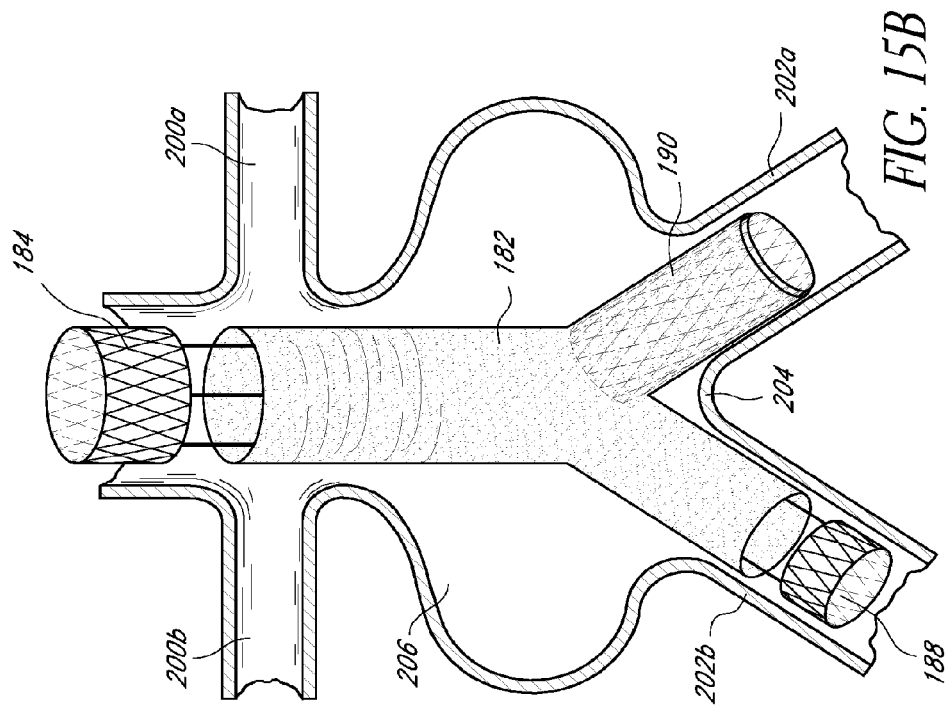
FIGS. 15A-15B and FIGS. 16A-16B illustrate the placement of the embodiment of the bifurcated stent graft in an abdominal aortic aneurysm.
Figure 15A:
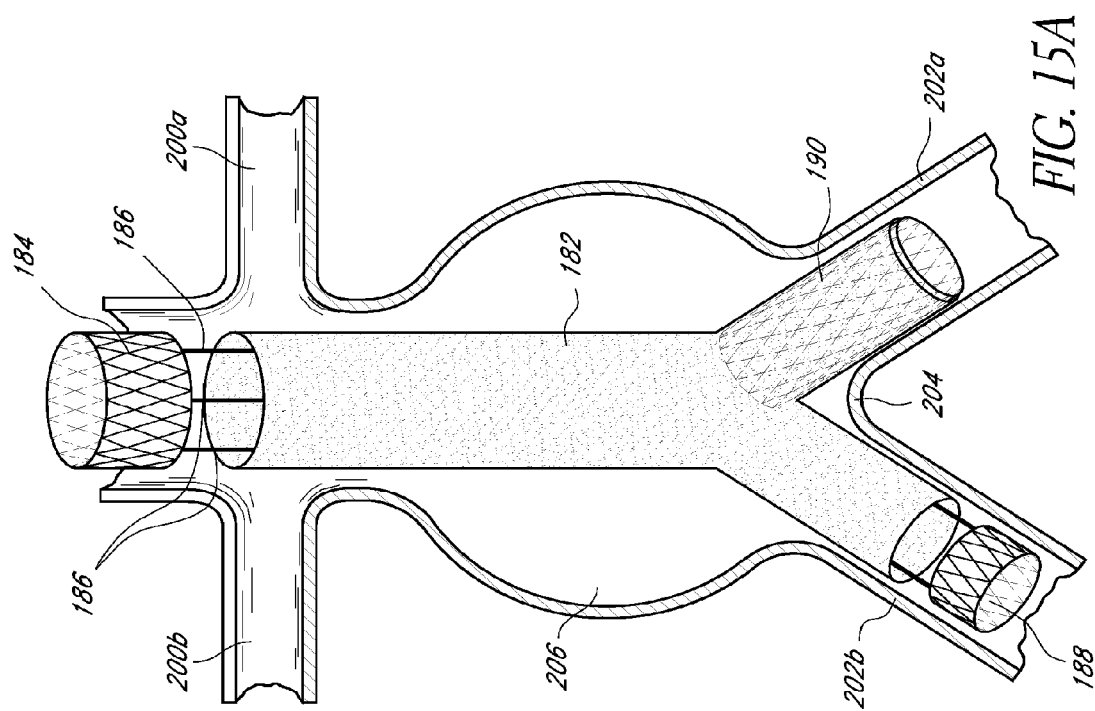
Figure 16B:
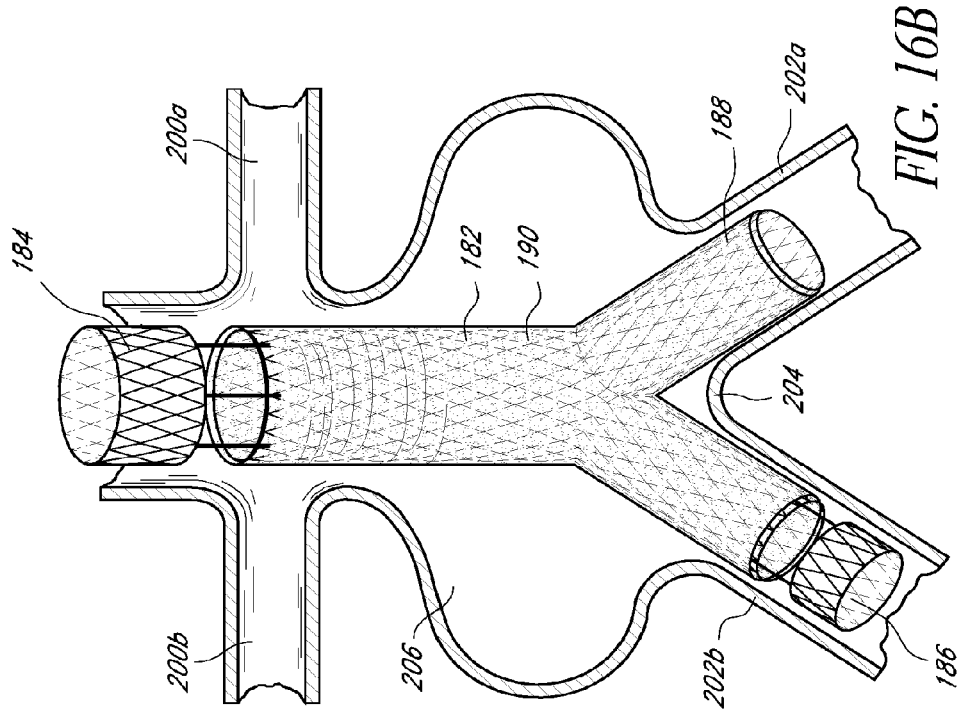
Figure 16A:
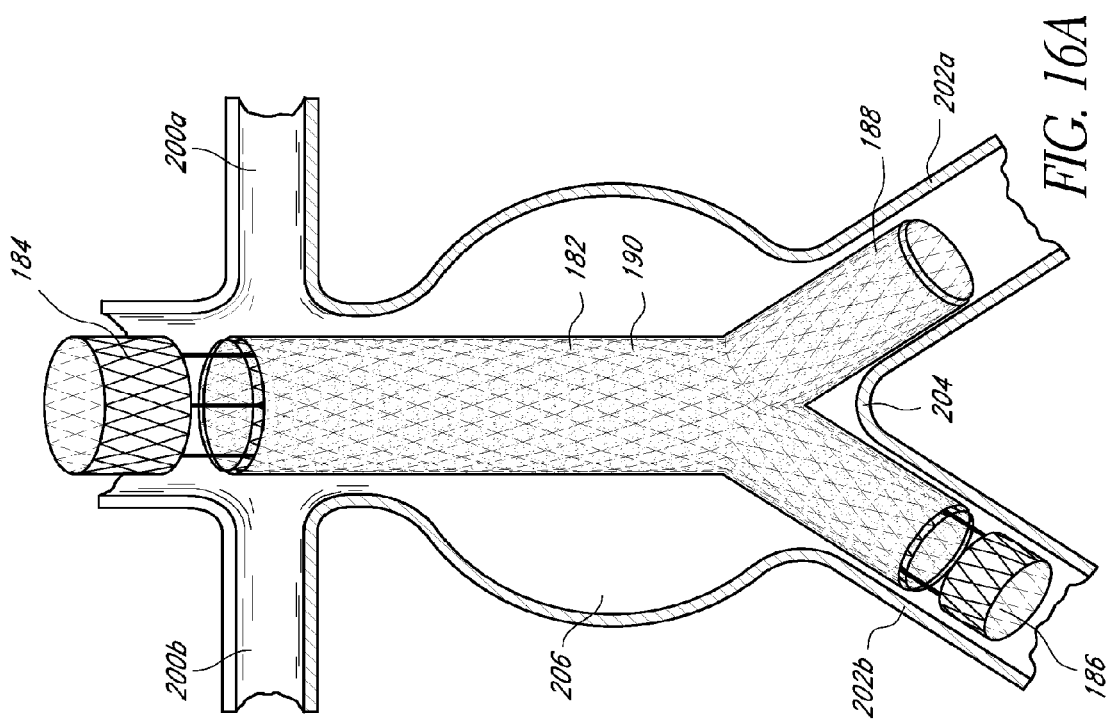

The main body of the graft and the two branch grafts can be deployed using any suitable delivery systems, including but not limited to the delivery systems described in U.S. Pat. No. 6,077,296 and/or U.S. patent application Ser. No. 12/101,863, which references are incorporated by reference in their entireties as if fully set forth herein. Because, in some embodiments, at least the proximal portion of the main body graft 182 is not axially supported by a stent, the graft 182 can be axially compressed to accommodate different lengths between the aortic bifurcation 204 and renal arteries 200a, 200b, as shown in FIG. 15B. As illustrated in FIGS. 16A and 16B, once the primary stent graft system has been deployed, the stent 190 can be introduced from the ipsilateral iliac artery 202b and deployed inside the graft 182 to provide additional support and fixation of the main body graft 182 and the ipsilateral branch graft.

While the above detailed description has shown, described, and pointed out novel features as applied to various embodiments, it will be understood that various omissions, substitutions, and changes in the form and details of the device or process illustrated can be made without departing from the spirit of the disclosure. Additionally, the various features and processes described above can be used independently of one another, or can be combined in various ways. All possible combinations and subcombinations are intended to fall within the scope of this disclosure.

As will be recognized, certain embodiments described herein can be embodied within a form that does not provide all of the features and benefits set forth herein, as some features can be used or practiced separately from others. The scope of the inventions is indicated by the appended claims rather than by the foregoing description. All changes which come within the meaning and range of equivalency of the claims are to be embraced within their scope.

For example, while some embodiments of the stent graft and delivery systems are described herein with respect to the abdominal aortic artery, the delivery and graft systems can be used for repairing vasculature in other portions of the body, including but not limited to the SMA, the inferior mesenteric artery, the thoracic artery, or any other arteries or blood vessels in the body suitable for such procedures or apparatuses.

What is claimed is:

1. A deployment system for deploying a stent graft within a passageway, comprising:
   a delivery catheter comprising an outer sheath, a proximal end, and a distal end;
   a stent having a first end and a second end, the stent being supported within the outer sheath at a first axial position in a collapsed state within the deployment system;
   a graft having a first end and a second end, the graft being supported within the outer sheath at a second axial position in a collapsed state within the deployment system;
   at least one connecting element extending from the second end of the stent to the first end of the graft so as to connect the second end of the stent to the first end of the graft; and
   one or more retraction elements attached to the graft, the one or more retraction elements extending to the proximal end of the delivery catheter, the one or more retraction elements being releasably attached to the second end of the graft;
   wherein the second axial position is different than the first axial position such that no substantial portion of the stent overlaps any portion of the graft while the stent and graft are in the collapsed state within the deployment system;
   wherein as the one or more retraction elements are retracted in a proximal direction the graft inverts and retracts so that at least a portion of the graft overlaps a portion of the stent in a deployed state.

2. The deployment system of claim 1, wherein the at least one connecting element comprises sutures, wires, strands, metal struts, or plastic struts.

3. The deployment system of claim 1, further comprising a second stent configured to be expandable within the graft.

4. The deployment system of claim 3, further comprising a third stent or stent segment configured to be expandable at least partially within the graft.

5. The deployment system of claim 1, wherein the graft is a bifurcated graft.

6. The deployment system of claim 1, wherein the one or more retraction elements are configured to invert and retract the graft before the stent is deployed within the passageway.

7. The deployment system of claim 1, wherein the one or more retraction elements are configured to invert and retract the graft so that substantially all of the graft overlaps the stent in the deployed state.

8. The deployment system of claim 1, wherein the graft is coaxially positioned relative to the stent.

9. The deployment system of claim 1, wherein at least one of the graft and the stent is tubular.

10. The deployment system of claim 1, wherein the graft comprises a main body, a first branch segment, and a second branch segment.

11. The deployment system of claim 10, further comprising a second stent supported in at least one of the first branch segment and the second branch segment.

12. The deployment system of claim 1, wherein the catheter further comprises an inner core, the inner core extending through the outer sheath and being axially moveable with respect to the outer sheath.

13. The deployment system of claim 1, wherein the stent is self-expandable.

14. The deployment system of claim 1, wherein the stent is balloon expandable.

\* \* \* \* \*